(12) United States Patent
Chang et al.

(10) Patent No.: US 8,399,416 B2
(45) Date of Patent: Mar. 19, 2013

(54) METHOD OF USING HEPARIN BINDING MOTIF FOR TREATING ASTHMA

(75) Inventors: Margaret Dah-Tsyr Chang, Hsinchu (TW); Tan-chi Fan, Hsinchu (TW); Shu-Chuan Lin, New Taipei (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 13/405,742

(22) Filed: Feb. 27, 2012

(65) Prior Publication Data

US 2012/0214730 A1 Aug. 23, 2012

Related U.S. Application Data

(60) Continuation-in-part of application No. 12/545,606, filed on Aug. 21, 2009, now abandoned, and a division of application No. 12/125,008, filed on May 21, 2008, now Pat. No. 7,595,374.

(51) Int. Cl.
*A61K 38/08* (2006.01)

(52) U.S. Cl. .................. 514/21.6; 514/826; 514/885

(58) Field of Classification Search ................. None
See application file for complete search history.

(56) References Cited

PUBLICATIONS

OA dated Sep. 28, 2011 from Taiwan Patent Office for corresponding Taiwan application 097145067.
Notification of Grant dated Jan. 19, 2012 from Taiwan Patent Office for corresponding Taiwan application 097145067.
Tan-chi Fan, and Margaret Dah-Tsyr Chang "Molecular Mechanisms of Cellular Binding and Endocytosis of Human Eosinophil Cationic Protein".
Ford J.G. et al., IL-13 and IFN-g: Interactions in Lung Inflammation, Journal of Immunology, 2001, pp. 1769-1777, 167.

*Primary Examiner* — Prema Mertz
(74) *Attorney, Agent, or Firm* — WPAT, P.C.; Anthony King

(57) ABSTRACT

The present invention is for an isolated peptide consisting of the amino acid sequence of SEQ ID NO: 9 and using the peptide for treating asthma by reducing cytotoxicity of eosinophil derived toxins in bronchial epithelial cells of the subject suffers from asthma. The method comprises preparing a pharmaceutical composition having the peptide of SEQ ID NO: 9 and administering an effective amount of the composition to the subject.

7 Claims, 19 Drawing Sheets

(A)

(B)

(C)

SEQUENCE LISTING

<160> NUMBER OF SEQ ID NOS: 9

<210> SEQ ID NO 1
<211> LENGTH: 27
<212> TYPE: DNA
<213> ORGANISM: Artificial
<220> FEATURE:
<223> OTHER INFORMATION: primer

<400> SEQUENCE: 1
tatgcagcgg cttgcgcaaa ccaaaat                    27

<210> SEQ ID NO 2
<211> LENGTH: 27

```
<212> TYPE: DNA
<213> ORGANISM: Artificial
<220> FEATURE:
<223> OTHER INFORMATION: primer

<400> SEQUENCE: 2
tttgcgcaag ccgctgcata attgtta                                              27

<210> SEQ ID NO 3
<211> LENGTH: 11
<212> TYPE: PRT
<213> ORGANISM: Artificial
<220> FEATURE:
<223> OTHER INFORMATION: Designed peptide based on Human ECP peptide
      with or without biotin-labeled on the 3' end.
<220> FEATURE:
<221> NAME/KEY: BINDING
<222> LOCATION: (1)..(11)

<400> SEQUENCE: 3

Asn Tyr Arg Trp Arg Cys Lys Asn Gln Asn Lys
1               5                   10

<210> SEQ ID NO 4
<211> LENGTH: 11
<212> TYPE: PRT
<213> ORGANISM: Artificial
<220> FEATURE:
<223> OTHER INFORMATION: Designed peptide based on Human EDN peptide
      with or without biotin-labeled on the 3' end.
<220> FEATURE:
<221> NAME/KEY: BINDING
<222> LOCATION: (1)..(11)

<400> SEQUENCE: 4

Asn Tyr Gln Arg Arg Cys Lys Asn Gln Asn Lys
1               5                   10

<210> SEQ ID NO 5
<211> LENGTH: 11
<212> TYPE: PRT
<213> ORGANISM: Artificial
<220> FEATURE:
<223> OTHER INFORMATION: Designed peptide based on Human RNase1 peptide
      with or without biotin-labeled on the 3' end.
<220> FEATURE:
<221> NAME/KEY: BINDING
<222> LOCATION: (1)..(11)

<400> SEQUENCE: 5

Met Thr Gln Gly Arg Cys Lys Pro Val Asn Lys
1               5                   10

<210> SEQ ID NO 6
<211> LENGTH: 12
<212> TYPE: PRT
<213> ORGANISM: Artificial
<220> FEATURE:
<223> OTHER INFORMATION: Designed peptide based on HIV-TAT peptide with
      or without biotin-labeled on the 3' end.
<220> FEATURE:
<221> NAME/KEY: BINDING
<222> LOCATION: (1)..(12)

<400> SEQUENCE: 6

Tyr Gly Arg Lys Lys Arg Arg Gln Arg Arg Lys
1               5                   10

<210> SEQ ID NO 7
<211> LENGTH: 6
```

```
<212> TYPE: PRT
<213> ORGANISM: Homo sapiens
<220> FEATURE:
<221> NAME/KEY: BINDING
<222> LOCATION: (1)..(6)

<400> SEQUENCE: 7

Gln Arg Arg Cys Lys Asn
1               5

<210> SEQ ID NO 8
<211> LENGTH: 5
<212> TYPE: PRT
<213> ORGANISM: Homo sapiens
<220> FEATURE:
<221> NAME/KEY: BINDING
<222> LOCATION: (1)..(5)

<400> SEQUENCE: 8

Arg Trp Arg Cys Lys
1               5

<210> SEQ ID NO 9
<211> LENGTH: 10
<212> TYPE: PRT
<213> ORGANISM: Homo sapiens
<220> FEATURE:
<221> NAME/KEY: BINDING
<222> LOCATION: (1)..(10)

<400> SEQUENCE: 9

Asn Tyr Arg Trp Arg Cys Lys Asn Gln Asn
1               5                   10
```

METHOD OF USING HEPARIN BINDING MOTIF FOR TREATING ASTHMA

CROSS-REFERENCE TO RELATED APPLICATIONS

This application is a Continuation-in-part of the pending U.S. patent application Ser. No. 12/545,606 filed on Aug. 21, 2009, which is a Divisional of the U.S. patent application Ser. No. 12/125,008 filed on May 21, 2008 now U.S. Pat. No. 7,595,374 for which priority is claimed and is incorporated herein by reference in its entirety.

Although incorporated by reference in its entirety, no arguments or disclaimers made in the parent application apply to this Continuation-in-part application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate.

FIELD OF THE INVENTION

The present invention relates to a heparin binding motif of eosinophil toxins and use thereof.

BACKGROUND OF THE INVENTION

Eosinophil cationic protein (ECP), a member of the ribonuclease A (RNase A) superfamily, is found in the specific granules of eosinophilic leukocytes. It is a single polypeptide with a molecular mass ranging from 16 to 21.4 kDa due to varying degrees of glycosylation. It shows a 67% amino acid sequence identity with eosinophil-derived neurotoxin (EDN), another eosinophil-secreted RNase. Although ECP shares the overall three-dimensional structure of RNase A, it has relatively lower RNase activity (Boix, E., et al. (1999) Journal of Biological Chemistry 274, 15605-15614). ECP released by activated eosinophils contributes to the toxicity against helminth parasites, bacteria, and single-strand RNA viruses (Lehrer, R., et al. (1989) Journal of Immunology 142, 4428-4434; Domachowske, J. B., et al. (1998) Nucleic acids research 26, 3358-3363). Together with other proteins secreted from eosinophils such as EDN, eosinophil peroxidase (EPO; also EPX), and major basic protein (MBP), ECP is thought to cause damage to epithelial cells, a common feature of airway inflammation in asthma (Gleich, G. J. (2000) Journal of Allergy and Clinical Immunology 105, 651-663).

The mechanism underlying the cytotoxic property of ECP is unclear. It has been hypothesized that ECP cytotoxicity is due to destabilization of lipid membranes of target cells (Young, J., et al. (1986) Nature 321, 613-616), and the degree of cytotoxicity is dependent on the cellular concentration (Carreras, E., et al. (2005) Molecular and Cellular Biochemistry 272, 1-7). The binding of ECP to target cells has been attributed to its high arginine content (estimated pI=10.8), which facilitates the interaction between ECP and negatively charged molecules on the cell surface (Carreras, E., et al. (2005) Molecular and Cellular Biochemistry 272, 1-7; Carreras, E., et al. (2003) Biochemistry 42, 6636-6644). Recently, we found that binding and endocytosis of ECP into bronchial epithelial cells were greatly dependent on the cell surface glycosaminoglycan (GAG), specifically heparan sulfate proteoglycans (HSPG) (Fan, T. C., et al. (2007) Traffic 8, 1778-1795). The cytotoxicity of ECP was severely reduced toward cell lines with heparan sulfate (HS) deficiency.

Heparin and HS are complex polysaccharides composed of alternating units of hexuronic acid and glucosamine. The uronic acid residues of heparin typically consist of 90% L-idopyranosyluronic acid and 10% D-glucopyranosyluronic acid (Capila, I. and Linhardt, R. J. (2002) Angewandte Chemie International Edition 41, 391-412). The N position of glucosamine may be substituted with an acetyl or sulfate group. The 3-O and 6-O positions of glucosamine and the 2-O of uronic acid may be sulfated. Through the combination of different negatively charged moieties, heparin and HS have been demonstrated to bind a variety of proteins with diverse functions, including growth factors, thrombin, chemokines and viral proteins. The HS chains contain domains with a high level of sulfation and epimerization (S-domains), regions with mixed N-acetylation and N-sulfation (NA/S-domains), and unmodified domains that are mostly N-acetylated and contain little sulfate (Tumova, S., et al. (2000). The international journal of biochemistry & cell biology 32, 269-288). Because HS chains contain heparin regions, heparin and its mimetics can be used to study interactions between proteins and polysaccharides.

The structure of ECP has been determined and refined to a resolution up to 1.75 Å, displaying a folding topology that involves three $\alpha$ helices and five $\beta$ strands (Mallorqui-Fernandez, G., et al. (2000) Journal of Molecular Biology 300, 1297-1307). The most interesting feature is the 19 surface-oriented arginine residues, conferring a strong basic character to ECP. However, the heparin binding site in ECP has not been identified. Heparin binding domains within proteins usually contain a high proportion of positively charged residues, which bind to the acidic groups of heparin through electrostatic interactions. It has been proposed that the three-dimensional structure of the HS chain is critical for protein binding (Hileman, R. E., et al. (1998) BioEssays 20, 156-167). However, not much is known about the three-dimensional structure of HS. After examining a series of heparin-binding protein sequences, Cardin and Weintraub proposed that the pattern XBBBXXBX or XBBXBX (where X represents hydrophobic or uncharged amino acids, and B represents basic amino acids) is responsible for HS binding to other proteins (Cardin, A. D. and Weintraub, H. J. (1989) Arteriosclerosis (Dallas, Tex. 9, 21-32). In addition, the following sequences have also been reported to serve as heparin binding motifs.

BBXXBBBXXBB (where B is a positively charge residue (arginine, lysine or hystidine) and X is any residue) (Olenina, L. V., et al. (2005) J Viral Hepat 12, 584-593).

BXXBBXB (where B is a basic residue and X is any residue) (Wu, H. F., et al. (1995) Blood 85, 421-428).

XBBBXXBBBXXBBX (where B is a basic residue and X is any residue) (Andersson, E., et al. (2004) Eur J Biochem 271, 1219-1226; Sobel, M., et al. (1992) The Journal of biological chemistry 267, 8857-8862).

TXXBXXTBXXXTBB (where B is a basic residue, X is any residue, and T defines a turn) (Capila, I. and Linhardt, R. J. (2002) Angewandte Chemie International Edition 41, 391-412; Hileman, R. E., et al. (1998) BioEssays 20, 156-167).

SUMMARY OF THE INVENTION

The present invention provides an isolated peptide consisting of the amino acid sequence of SEQ ID NO: 9.

The present invention further provides a method for treating asthma of a subject comprising preparing a pharmaceutical composition having the peptide of SEQ ID NO: 9 and administering an effective amount of the composition to the subject.

DETAILED DESCRIPTION OF THE INVENTION

Figure 1:
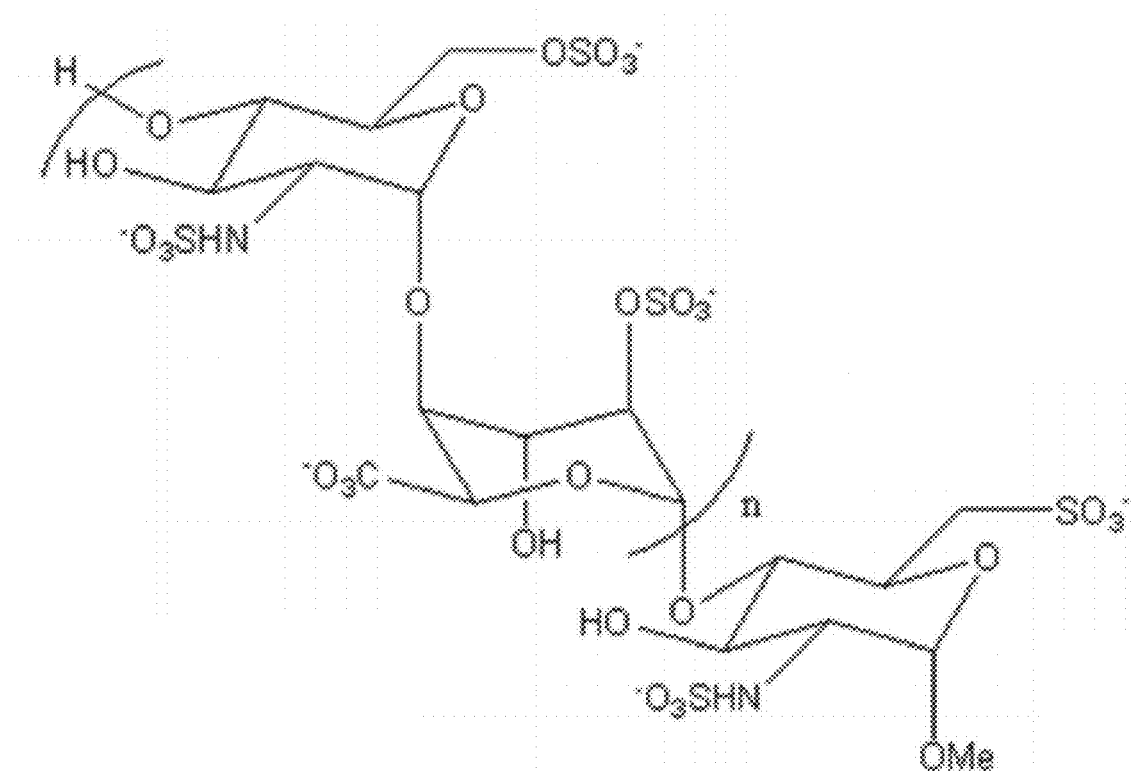
FIG. 1. The structure of synthetic heparin oligosaccharides used in the present invention. n=1-4 (n=1, dp3; n=2, dp5; n=3, dp7; n=4, dp9).

The term "eosinophil derived toxins" used herein means the toxins derived from eosinophil and damage cells when the toxins are entered into the cells. The species of eosinophil derived toxins include but is not limited to eosinophil cationic protein (ECP), eosinophil-derived neurotoxin (EDN), eosinophil peroxidase (EPO, also called EPX), and major basic protein (MBP).

In the present invention, a linear heparin binding site on ECP and the shortest ECP-binding heparin oligosaccharide unit have been identified. Loop L3 of ECP mediates the interaction between ECP and cell surface HSPG, contributing to ECP cytotoxicity. Furthermore, the dissociation constants between oligosaccharides and ECP were determined by tryptophan emission titration.

Accordingly, the present invention provides a heparin binding motif comprising BZBXBX, wherein X represents any amino acid, Z represents an aromatic amino acid and B represents a basic amino acid. The present invention also provides a heparin binding motif of eosinophil cationic protein comprising the above sequence. In the more embodiment of the present invention, the said motif is SEQ ID NO: 8.

The present invention further provides a method for reducing cytotoxicity of eosinophil derived toxins comprising administering to a subject an effective amount of heparin, heparan sulfate, potent heparanase inhibitor or a polypeptide which has sequence as follows: BZBXBX, XBBBXXBX, XBBXBX, BBXXBBBXXBB, BXBBXB, XBBBXX-BBBXXBBX, or TXXBXXTBXXXTBB, wherein X represents any amino acid, Z represents an aromatic amino acid, B represents a basic amino acid and T represents a turn. The said subject is mammalian. The said polypeptide comprises a high portion of positively charged residues. In the embodiment of the present invention, the polypeptide comprises QRRCKN (SEQ ID NO:7) or RWRCK (SEQ ID NO:8). In the more embodiment of the present invention, the polypeptide is SEQ ID NO: 3 (NYRWRCKNQNK) or SEQ ID NO: 4 (NYQR-RCKNQNK). The said heparin comprises low molecular weight heparin (LMWH, Sigma-Aldrish, average MW 3,000), high molecular weight heparin (HMWH, Sigma-Aldrish, average MW 16,000), heparan sulfate proteoglycans (HSPG) or synthetic heparin oligosaccharides and heparan sulfates from the degree of polymerization (dp) of 3 to 15. In the embodiment of the present invention, the synthetic heparan sulfates comprises degree of polymerization (dp) 5 to 9 (dp 3 to dp 9: MW 926-2,642; Molecular formula: P+nQ where P is a 2 methoxy-glucosamine, Q represents disaccharide units consisted of hexuronic acid and glucosamine, and n is an integral. The molecular weight of X is 349 and that of Y ranges from 333 to 573. Furthermore, the glucosamine of P could be substituted by other protecting group).

The cytotoxicity of eosinophil derived toxins is reduced by reducing endocytosis of eosinophil derived toxins such as ECP, EDN, EPO, and MBP. The method can further inhibit asthma. The said asthma includes ECP/EDN-related asthma, cytotoxic RNase-related asthma and high pI toxin-related asthma.

The present invention provides an isolated peptide consisting of the amino acid sequence of SEQ ID NO: 9, which is a heparin binding site of eosinophil cationic protein (ECP) and has heparin or heparan sulfate binding activity.

The present invention also provides a method for treating asthma of a subject, comprising preparing a pharmaceutical composition comprising the peptide of SEQ ID NO: 9 and administering an effective amount of the composition to the subject.

The asthma includes ECP/EDN-related asthma, cytotoxic RNase-related asthma and high pI toxin-related asthma and is treated by reducing cytotoxicity of eosinophil derived toxins in bronchial epithelial cells of the subject. The cytotoxicity of eosinophil derived toxins is reduced by reducing endocytosis of eosinophil derived toxins such as ECP, EDN, EPO, and MBP. The reducing endocytosis of eosinophil derived toxins is achieved by the peptide of SEQ ID NO: 9 compete with eosinophil derived toxins for cellular binding.

In the present invention, the composition can further comprise a pharmaceutically acceptable carrier and is administrated intranasal. In the preferred embodiment of the present invention, the subject is a mammal, and in the more preferred embodiment, the subject is a human.

EXAMPLE

Example 1

Materials

Mouse anti-MBP (maltose binding protein) was obtained from Santa Cruz Biotechnology (Santa Cruz, Calif.). RNase A was purchased from Promega (Madison, Wis.). Chemicals were purchased from Sigma-Aldrich (St. Louis, Mo.) unless otherwise specified. Human ECP peptide NYRWRCKN-QNK-biotin (C1, SEQ ID NO: 3), EDN peptide NYQRRCK-NQNK-biotin (D1, SEQ ID NO: 4), RNase1 peptide MTQGRCKPVNK-biotin (R1, SEQ ID NO: 5), and HIV-TAT peptide YGRKKRRQRRRK-biotin (TAT, SEQ ID NO: 6) were purchased from Genemed Synthesis (South San Francisco, Calif.).

Statistical analysis Data were expressed as mean±standard deviation (SD). Analysis was performed with Mann-Whitney U test for comparison of two groups. Differences with a probability value <0.05 were considered significant. Analysis were performed using Statistical Package for the Social Sciences (version 10.1; SPSS, Chicago, Ill., USA).

Example 2

Oligosaccharide Length-Dependence of ECP-Heparin Interaction

Recombinant hECP containing a C-terminal $His_6$ tag was expressed in *E. coli* BL21-CodonPlus (DE3) (Novagen, Madison, Wis.), purified by chromatography, and refolded as previously described (Boix, E., et al. (1999) Journal of Biological Chemistry 274, 15605-15614). MBP-ECP was purified using amylase affinity chromatography.

The prior art demonstrated that binding and endocytosis of ECP are HSPG dependent (Fan, T. C., et al. (2007) Traffic 8, 1778-1795). An early study demonstrated ECP purification using heparin-Sepharose chromatography (Gleich, G. J., et al. (1986) Proc Natl Acad Sci USA 83, 3146-3150). Thus, the minimal heparin length (or disaccharide unit) required to interact with ECP was investigated by FACE (Fluorescence-assisted carbohydrate electrophoresis).

Synthetic heparin oligosaccharide (FIG. 1) (Lee, C. J., et al. (2004) J Am Chem Soc 126, 476-477), low molecular weight heparin (LMWH) and PI-88 (kindly provided by Progen Inc., Australia) were labeled with 2-aminoacridone (AMAC) as described (Calabro, A., et al. (2000) Glycobiology 10, 273-281). AMAC-oligosaccharide and proteins were incubated at room temperature for 15 min, loaded onto 1% gels and electrophoresed as described (Holmes, O., et al. (2007) J Mol Biol 367, 395-408).

Figure 2:
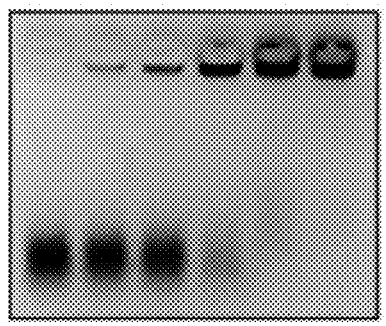
FIG. 2. FACE analysis to evaluate binding of ECP to various sugar-containing substrates. A, AMAC-labeled LMWH was incubated with or without ECP in PBS for 10 min at 25° C., and the binding reaction products were separated on a 1% agarose gel. The numbers above the gel indicate the molar ratio of ECP to LMWH. B, Representative oligosaccharide binding pattern of ECP. AMAC-labeled heparin dp3 (10.8 nmol), dp5 (3.3 nmol), dp7 (1.4 nmol), dp9 (1.1 nmol), LMWH (0.03 nmol) and PI-88 (0.03 nmol) were incubated with or without 10-fold molar excess of ECP, and the binding reaction products separated on a 1% agarose gel. C, Representative oligosaccharide binding pattern of EDN. AMAC-labeled heparin dp3 (10.8 nmol), dp5 (3.3 nmol), dp7 (1.4 nmol), dp9 (1.1 nmol), LMWH (0.03 nmol) and PI-88 (0.03 nmol) were incubated with or without 10-fold molar excess of ECP, and the binding reaction products separated on a 1% agarose gel.
Figure 2:
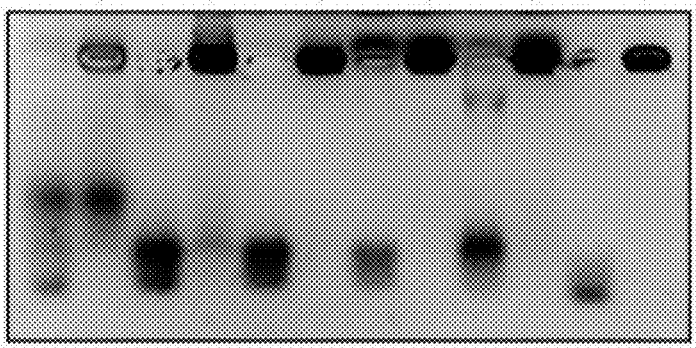
Figure 2:
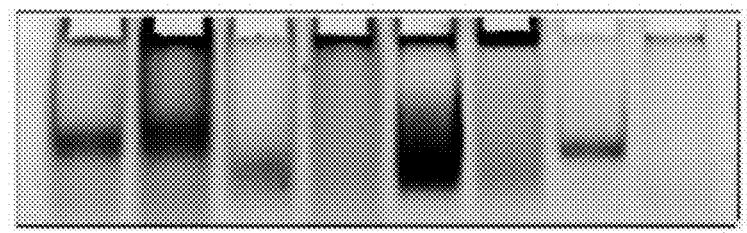

Initially, ECP was co-incubated with LMWH at various molar ratios, and the binding products were analyzed by gel electrophoresis. The decrease in the free LMWH signal was monitored as ECP concentration was increased (FIG. 2A). Subsequently, the dependence of ECP binding on heparin oligosaccharide size was examined in the presence of synthetic heparin oligosaccharides from the degree of polymerization (dp) 3 to 9 using LMWH as a positive control. It was apparent that dp5 served as the shortest heparin fragment that retained the ability to bind ECP (FIG. 2B). Furthermore, we tested a potent heparanase inhibitor (PI-88), undergoing clinical trials for its anti-angiogenic and anti-metastatic effects (Joyce, J. A., et al. (2005) Oncogene 24, 4037-4051; Parish, C. R., et al. (1999) Cancer research 59, 3433-3441), that contains a mixture of highly sulfated mannose-containing di- to hexasaccharides (Yu, G., et al. (2002) European journal of medicinal chemistry 37, 783-791; Ferro, V., Li, C., et al. (2002) Carbohydrate research 337, 139-146). Interestingly, this heparin mimetic could also bind ECP (FIG. 2B). In addition, similar results were observed for EDN (FIG. 2C).

Example 3

Competitive Inhibition of ECP Binding to Cells by Synthetic Oligosaccharides

Beas-2B, a human bronchial epithelial cell line, was cultured in RPMI 1640 medium (Sigma-Aldrich) supplemented with heat-inactivated 10% fetal bovine serum (Gibco/Invitrogen, Carlsbad, Calif.).

The ability of MBP-ECP to bind cells in the presence of serial dilutions of oligosaccharides or peptides was determined as described (Fan, T. C., et al. (2007) Traffic 8, 1778-1795). At the present invention, synthetic heparins (dp3-9) were tested for their ability to interfere with ECP binding to Beas-2B cells. Briefly, confluent monolayers of Beas-2B cells in 96-well plates were pretreated with various concentrations of oligosaccharides or peptides in serum-free RPMI 1640 medium at 4° C. for 30 min before incubation with 5 μg/ml MBP-ECP at 4° C. for 1 h. The cells were then washed with ice-cold PBS and fixed with 2% PFA at room temperature for 15 min prior to blocking with 2% BSA/PBS at room temperature for 90 min. The level of bound MBP-ECP was quantified by ELISA analysis. MBP-ECP was detected using mouse monoclonal anti-MBP and goat anti-mouse horseradish peroxidase (HRP)-conjugated secondary antibody, followed by the enhanced chemiluminescence detection system. The amount of MBP-ECP bound to cells without oligosaccharide or peptide treatment was set to 100%.

Figure 3:
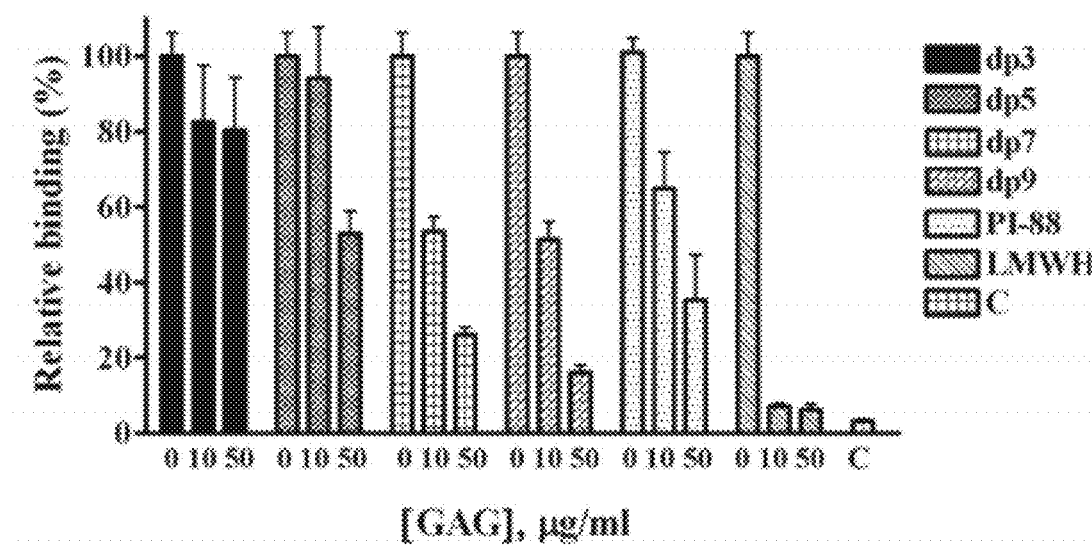
FIG. 3. Heparin oligosaccharides inhibit ECP binding to cells. Beas-2B cells were preincubated with heparin of different sizes in RPMI 1640 medium for 30 min at 4° C. before incubation with MBP-ECP for an additional 1 h. After treatment, the cells were washed with PBS and fixed with PFA. The level of bound MBP-ECP was assessed by ELISA. The amount of MBP-ECP bound to cells without GAG treatment was set to 100%. C, control (cells were incubated with MBP.) The data shown are the means of triplicate experiments.

Beas-2B cells were preincubated with oligosaccharides, and bound ECP was detected essentially as described (Fan, T. C., et al. (2007) Traffic 8, 1778-1795). The degree of inhibition increased with increasing oligosaccharide length (FIG. 3). Fifty micrograms per milliliter of heparin dp5 inhibited 50% of ECP binding to cells, and the same amount of dp7 and dp9 was capable of inhibiting over 70% and 80% of ECP binding, respectively. These data revealed that pentasaccharide was the minimal length sufficient to interfere with ECP binding to Beas-2B cells. In addition, the concentration dependence of PI-88 against cellular binding of ECP was similar to that of dp7 (FIG. 3).

Example 4

Identification of Heparin-Binding Sequence in ECP

A consensus sequence of the heparin binding site (e.g., XBBXBX or XBBBXXBX) has been found in many GAG-binding proteins or peptides (Hileman, R. E., et al. (1998) BioEssays 20, 156-167; Cardin, A. D. and Weintraub, H. J. (1989) Arteriosclerosis Dallas, Tex. 9, 21-32). Inspection of the sequences of human RNase A family members revealed a surface loop L3 region, $^{34}$QRRCKN (SEQ ID NO: 7), in EDN that exactly matches the XBBXBX motif (FIG. 4A), but no consensus heparin-binding motif was found in ECP. Therefore, it was speculated that residues 34-38 ($^{34}$RWRCK, SEQ ID NO: 8) in ECP that correspond to the consensus motif in EDN might also bind heparin. To determine whether this region contributes to cellular binding, cell ELISA analysis was conducted using MBP-ECP and MBP-ECP mt1 containing the mutations R34A/W35A/R36A/K38A.

Figure 4:
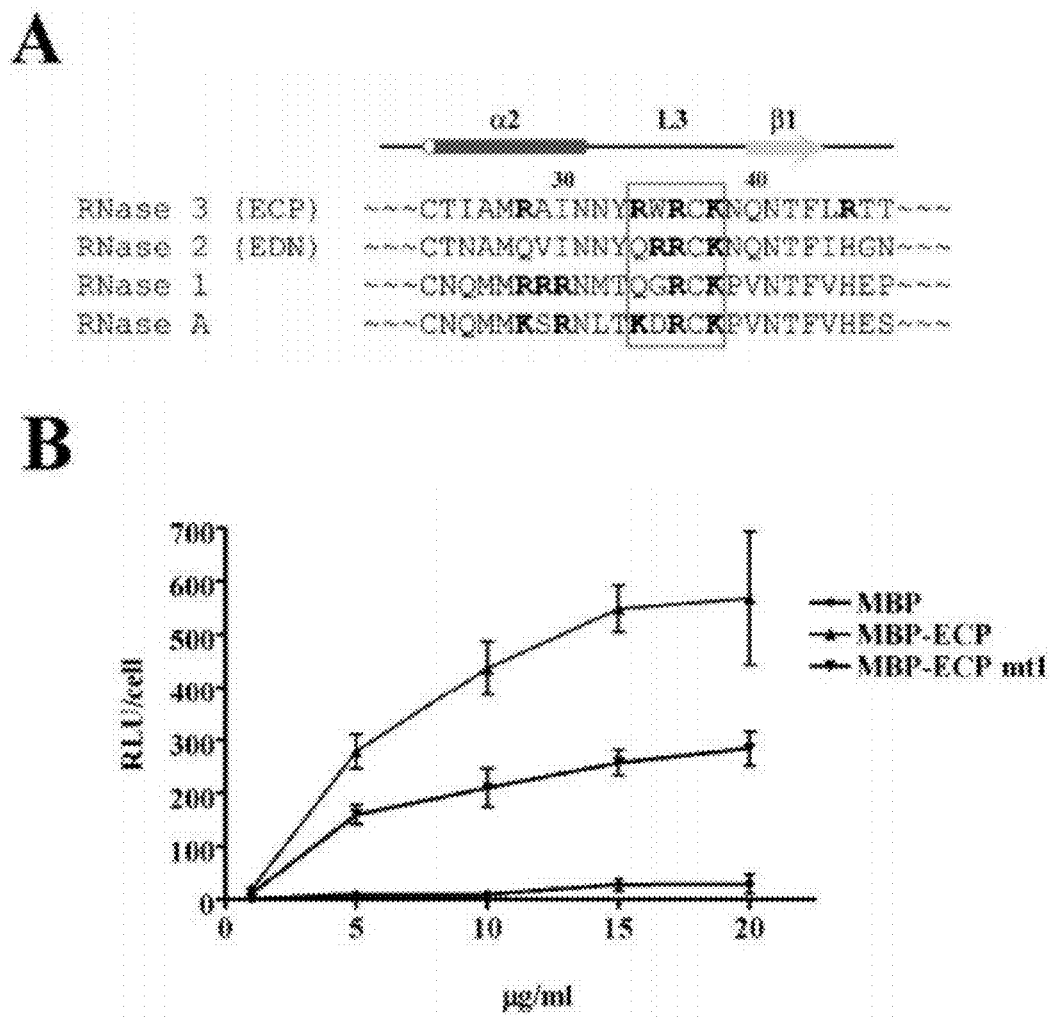
FIG. 4. Identification of the heparin binding site in ECP. A, Alignment of human and bovine RNases. The sequences between α2 and β1 of the RNases are aligned. Regions in other RNases that are highly similar to the putative heparin binding site of ECP are boxed. Positively charged amino acids are indicated in bold. B, Beas-2B cells were incubated with MBP-ECP for 1 h at 4° C. The amount of MBP-ECP bound to cells was assessed as for FIG. 3.

Amino acid residues R34, W35, R36, and K38 of ECP were simultaneously substituted to alanine using QuickChange site-directed mutagenesis (Stratagene, La Jolla, Calif.) and the resultant mutant was named ECP mt1. The primers used were as follows: mt1 forward, 5'-TATGCAGCGGCTTGCG-CAAACCAAAAT-3' (SEQ ID NO: 1), and mt1 reverse, 5'-TTTGCGCAAGCCGCTGCATAATTGTTA-3' (SEQ ID NO: 2). E. coli BL21-CodonPlus(DE3) cells were used to transform various plasmids. This mutant had only 50% of the cell-binding activity, indicating the importance of the $^{34}$RWRCK motif in ECP for cellular HS binding (FIG. 4B).

Example 5

Characterization of Association Between ECP and Heparin Oligosaccharides

The binding affinities of wild-type and mutant ECP for heparin oligosaccharides were subsequently monitored by intrinsic tryptophan fluorescence titration (Lau, E. K., et al. (2004) The Journal of biological chemistry 279, 22294-22305).

Binding of ECP to heparin was monitored by changes in intrinsic tryptophan fluorescence emission (IFTE). ECP (200 nM) in PBS at 25° C. was titrated with small aliquots of a high concentration of pentasaccharides with minimal dilution (<2%). Protein fluorescence measurements were recorded 2 min after each addition on a Hitachi 8000 spectrofluorimeter at emission wavelength of 340 nm using an excitation wavelength of 280 nm. ΔF, the relative fluorescence change, equals $F_0-F_{obs}$, where $F_0$ and $F_{obs}$ represent the initial and observed fluorescence values, respectively. Binding constants were estimated from the titration data using a nonlinear least-squares computer fit to the equation based on 1:1 binding stoichiometry (Venge, P. and Bystrom, J. (1998) The international journal of biochemistry & cell biology 30, 433-437):

$$\Delta F = \Delta F_{max} \times ([P]+[H]+K_d-(([P]+[H]+K_d)^2-4\times[P]\times[H])^{1/2})/(2\times[P]) \qquad \text{(Eq. 1)}$$

where $\Delta F_{max}$ is the maximum relative fluorescence change, P is the total concentration of ECP, H is the concentration of heparin, and $K_d$ is the dissociation constant for the ECP-heparin interaction.

Figure 5:
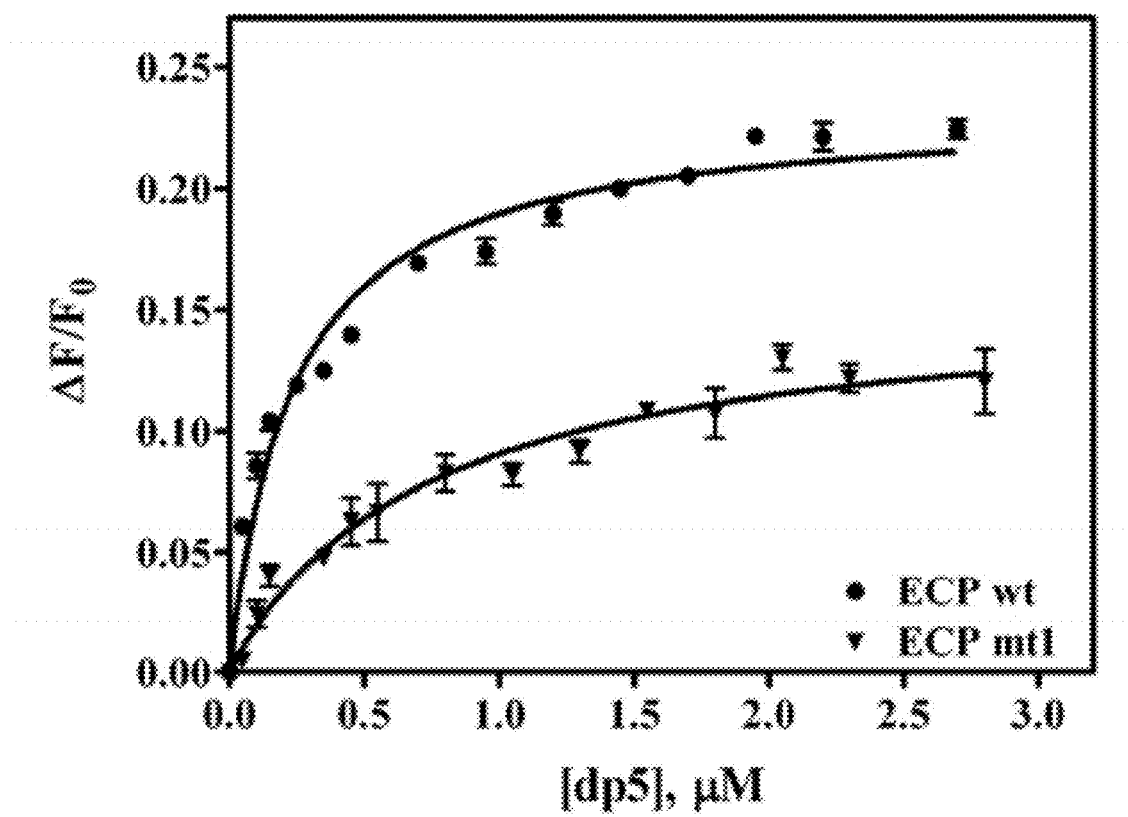
FIG. 5. ITFE profiles of ECP wt and mt1 with dp5. Tryptophan titration emission spectra of 0.2 mM ECP wt or mt1 bound with dp5. The emission spectra at 340 nm were recorded. The resulting isotherms were fitted by nonlinear regression least-squares computer fit using the KaleidaGraph Synergy Software. ΔF, the relative fluorescence change, equals $F_0-F_{obs}$, where $F_0$ and $F_{obs}$ represent the initial and observed fluorescence values, respectively.

The change in tryptophan fluorescence revealed that wild-type ECP bound to dp5 with high affinity, and the corresponding $K_d$ was 139.6 nM (FIG. 5). As expected, a 4- to 5-fold increase in $K_d$ to 568.1 nM was observed for ECP mt1 (R34A/W35A/R36A/K38A) (Table I), indicating decreased heparin binding activity for mutant ECP lacking the key heparin binding motif in the L3 region.

TABLE I

Dissociation constant ($K_d$) determination for wild-type ECP and mt1 with heparin oligosaccharides.

| Oligosaccharide | ECP wt $K_d$ (nM) | ECP mt1 $K_d$ (nM) |
|---|---|---|
| dp9 | 62.6 | 400.3 |
| dp5 | 139.6 | 568.1 |

$K_d$ was measured in PBS at 25° C. The change in intrinsic tryptophan fluorescence was fit by the equation 1 to obtain $K_d$.

Figure 6:
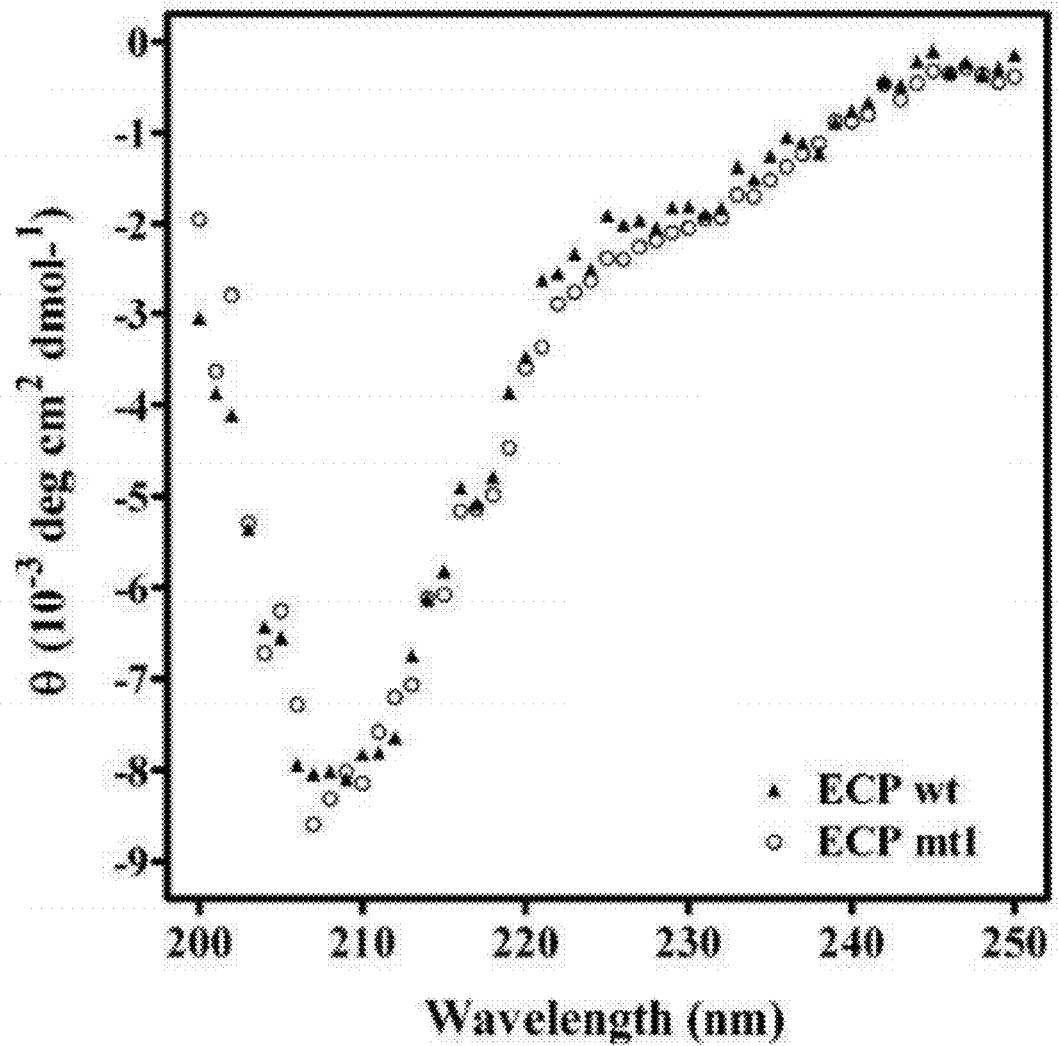
FIG. 6. CD spectra of ECP wt and mt1. The CD spectra were scanned from 200 to 260 nm.

Circular dichroism spectroscopy (CD spectroscopy) was used to compare the conformations of wild-type ECP and ECP mt1. CD spectra were recorded using an Aviv model 202 CD Spectrometer equipped with a 450-watt Xenon arc lamp. Far-UV spectra were recorded at 25° C. from 200 to 250 nm using a 0.1-cm cuvette containing 10 µM protein in PBS. The CD spectra were recorded at 1.5-min intervals with a bandwidth of 1 nm. Each spectrum is an average of three consecutive scans and was corrected by subtracting the buffer spectrum. The results showed that the secondary structure of ECP mt1 was very similar to that of wild-type ECP (FIG. 6). These results strongly indicated that the decrease in heparin binding affinity resulted from a loss of the specific recognition sequence motif, and not a conformational change in ECP mt1.

Example 6

Competitive Inhibition of ECP Binding to Cells by Synthetic Peptides

Figure 7:
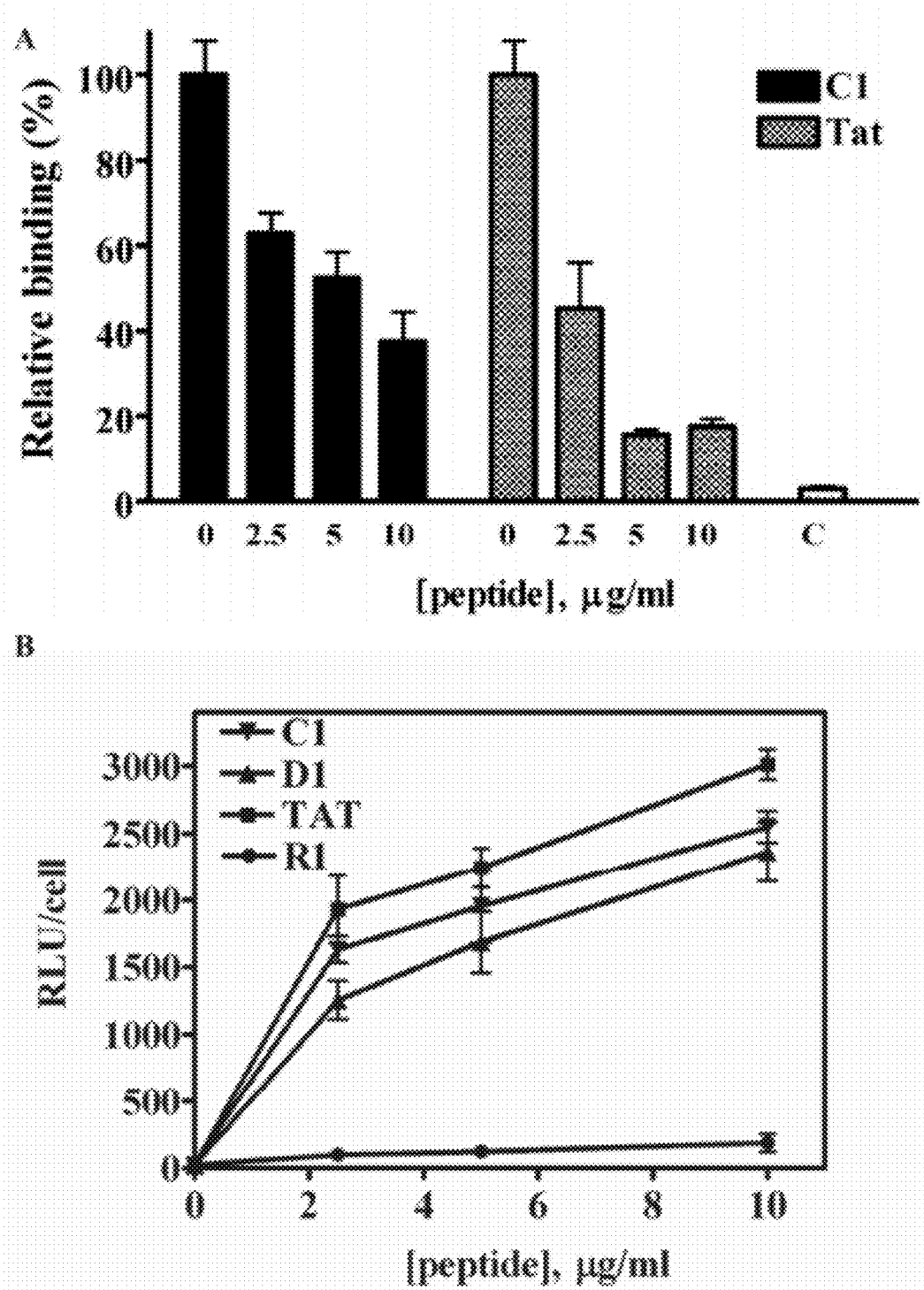
FIG. 7. Synthetic peptides inhibit ECP binding to cells. A, Beas-2B cells were preincubated with peptides in RPMI 1640 medium for 30 min at 4° C. before incubation with MBP-ECP for an additional 1 h. After treatment, the cells were washed with PBS and fixed with PFA. The level of bound MBP-ECP was assessed by ELISA. The amount of MBP-ECP bound to cells without peptide treatment was set to 100%. The data shown are the means of triplicate experiments. B, Beas2-B cells were incubated with biotinylated peptides for 1 h at 4° C. The amount of peptides bound to cells was assessed as for FIG. 3.

To investigate whether the RWRCK (SEQ ID NO: 8) motif is directly responsible for heparin binding, cell ELISA was conducted using a synthetic peptide, C1 (SEQ ID NO: 3), along with a positive control peptide derived from HIV-TAT, TAT (SEQ ID NO: 6) (Vives, E., et al. (1997) The Journal of biological chemistry 272, 16010-16017; Ziegler, A. and Seelig, J. (2004) Biophysical journal 86, 254-263). The dose-dependent competition of these peptides is shown in FIG. 7A. Binding of MBP-ECP to cell-surface HS was significantly reduced in the presence of both C1 (SEQ ID NO: 3) and TAT (SEQ ID NO: 6) peptides. Therefore, synthetic peptides with heparin binding activity may compete with ECP for cellular binding. Furthermore, the cell surface binding ability of peptides was tested using cell ELISA assay. As expected, similar to the TAT (SEQ ID NO: 6), C1 (SEQ ID NO: 3), and D1 (SEQ ID NO: 4) peptides bound to the cell surface, whereas R1 (SEQ ID NO: 5) peptide was devoid of such function (FIG. 7B).

Example 7

Interaction Between Synthetic Heparin Binding Peptide and Cell Surface

To investigate whether the heparin binding QRRCK motif on EDN, corresponding to the "RWRCK" motif on ECP (SEQ ID NO: 8), was directly responsible for heparan sulfate binding on cell surface, Beas-2B cell-peptide binding was conducted using a synthetic peptide, D1 (SEQ ID NO: 4), and a positive control, TAT (SEQ ID NO: 6) purchased from Genemed Synthesis (South San Francisco, Calif.). The data demonstrated that synthetic peptide D1 (SEQ ID NO: 4) bound to Beas-2B cell surface heparan sulfate at low temperature, in consistent with the results obtained from cell-ELISA competitive inhibition experiments shown in FIG. 8.

Example 8

Interaction of Synthetic Peptides with LMWH

Figure 8:
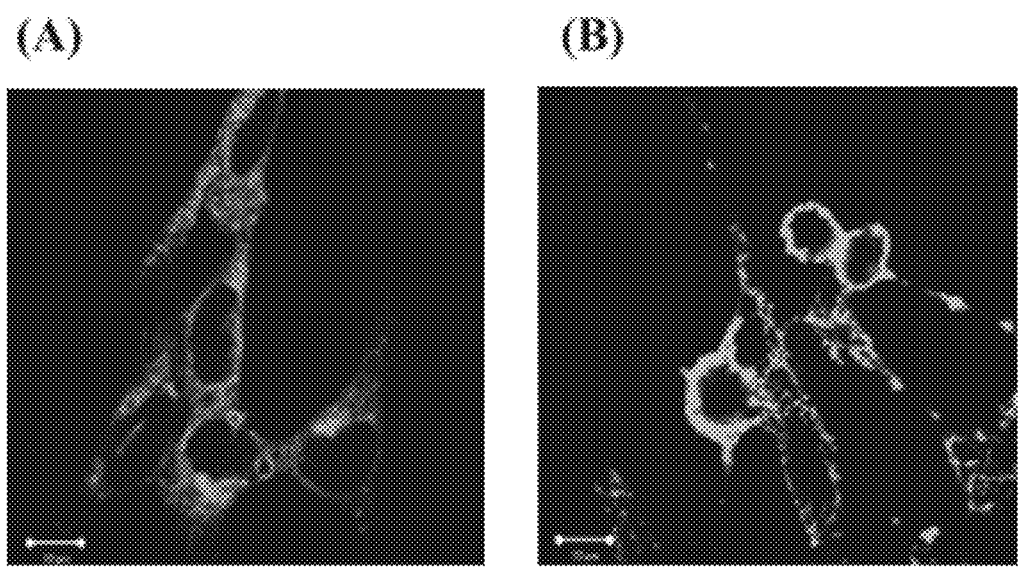
FIG. 8. Heparin-binding synthetic peptides. Human Beas-2B cells were incubated with synthetic peptide (A, TAT; B, D1) at 4° C. for 30 min and then washed, fixed and analyzed. Synthetic peptide was identified with mouse anti-biotin monoclonal antibody and FITC-conjugated goat anti-mouse antibody. The distribution of synthetic peptide was examined by confocal microscopy. Scale bar, 10 mm.
Figure 9:
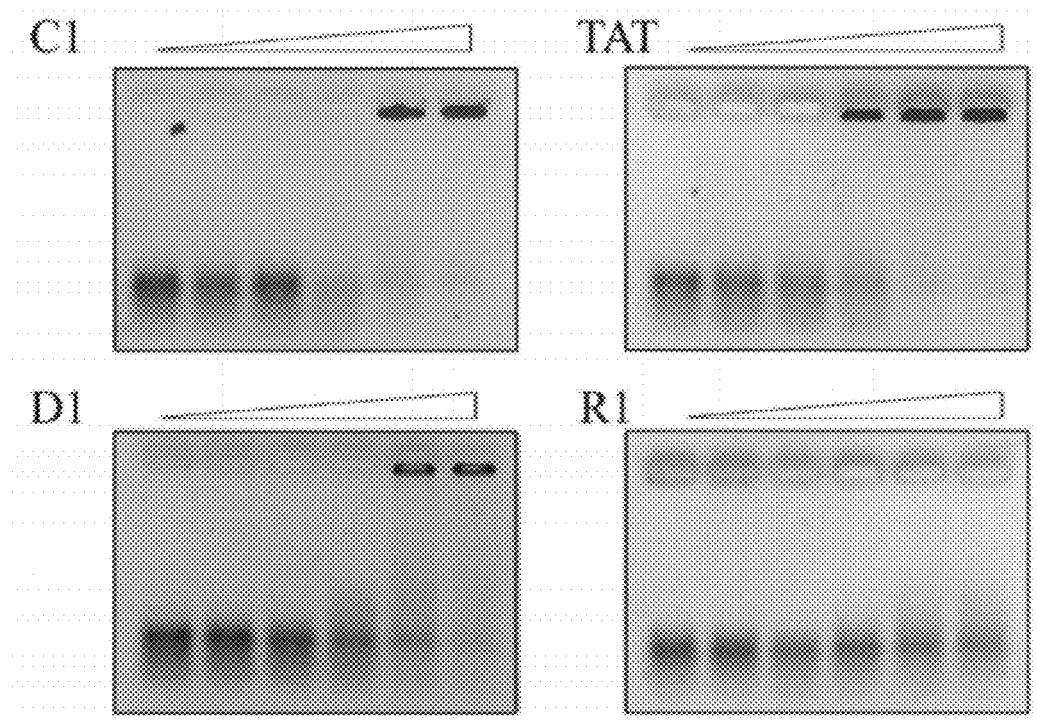
FIG. 9. FACE analysis of synthetic peptides. AMAC-labeled LMWH were incubated without or with increasing concentrations of C1, TAT, D1 and R1 peptides at room temperature for 15 min. Samples were loaded and separated by agarose gel electrophoresis as described for FIG. 2.

The ability of C1 (SEQ ID NO: 3) to directly interact with LMWH was further investigated by FACE analysis. As expected, a decreased amount of free AMAC-LMWH signal was observed with increasing concentration of C1 (SEQ ID NO: 3) peptide or TAT (SEQ ID NO: 6) peptide (FIG. 9). In addition, because EDN contains a conventional heparin binding sequence, the corresponding peptide, D1 (SEQ ID NO: 4),
was also synthesized and tested. As shown in FIG. 8, D1 (SEQ ID NO: 4) bound heparin as tightly as C1 (SEQ ID NO: 3). Interestingly, although the peptide segment in the corresponding location of human RNase 1 (R1, SEQ ID NO: 5) also contains several positively charged residues, it did not bind heparin. Taken together, these results indicate that the RWRCK (SEQ ID NO: 8) motif within loop L3 of ECP serves as a specific heparin binding site.

Example 9

Characterization of Association Between C1 and Heparin Oligosaccharides

Figure 10:
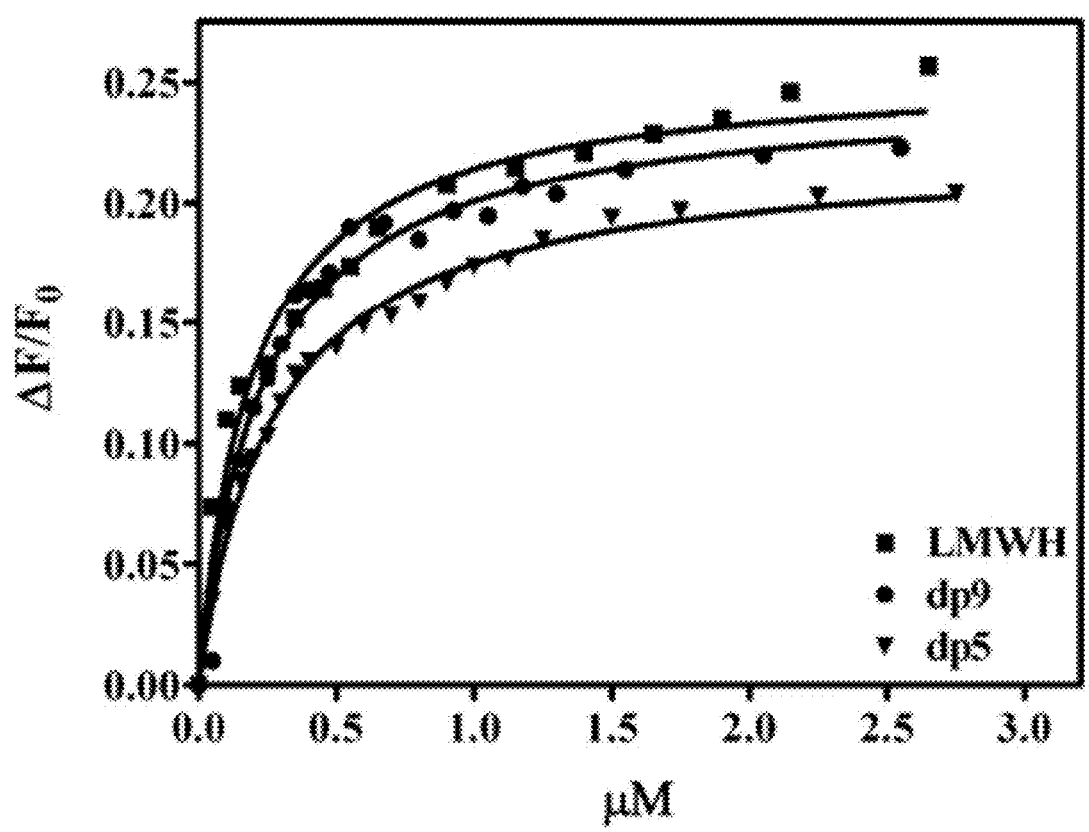
FIG. 10. Titration profiles of synthetic peptides by synthetic heparin oligosaccharides. Titrations were carried out on 1 μM peptides in the presence of heparin oligosaccharides. The $K_d$ of each peptide-oligosaccharide interaction was determined by measuring the fluorescence change of intrinsic tryptophan at 340 nm. Data were fitted to a single-binding-site curve using nonlinear least-squares analysis.

The definitive heparin binding activity of the C1 (SEQ ID NO: 3) peptide was determined by ITFE, which clearly demonstrated that C1 has high affinity for heparin (FIG. 10). The $K_d$ values obtained for LMWH, dp9, and dp5 binding to the C1 (SEQ ID NO: 3) peptide were 192.0, 229.1, and 274.8 nM, respectively (Table II), indicating that C1 (SEQ ID NO: 3) bound tighter to longer heparin oligosaccharides.

TABLE II

Determination of dissociation constants ($K_d$) for C1 peptide with heparin oligosaccharides.

| Oligosaccharide | $K_d$ (nM) |
|---|---|
| LMWH | 192.0 |
| dp9 | 229.1 |
| dp5 | 274.8 |

Example 10

Figure 11:
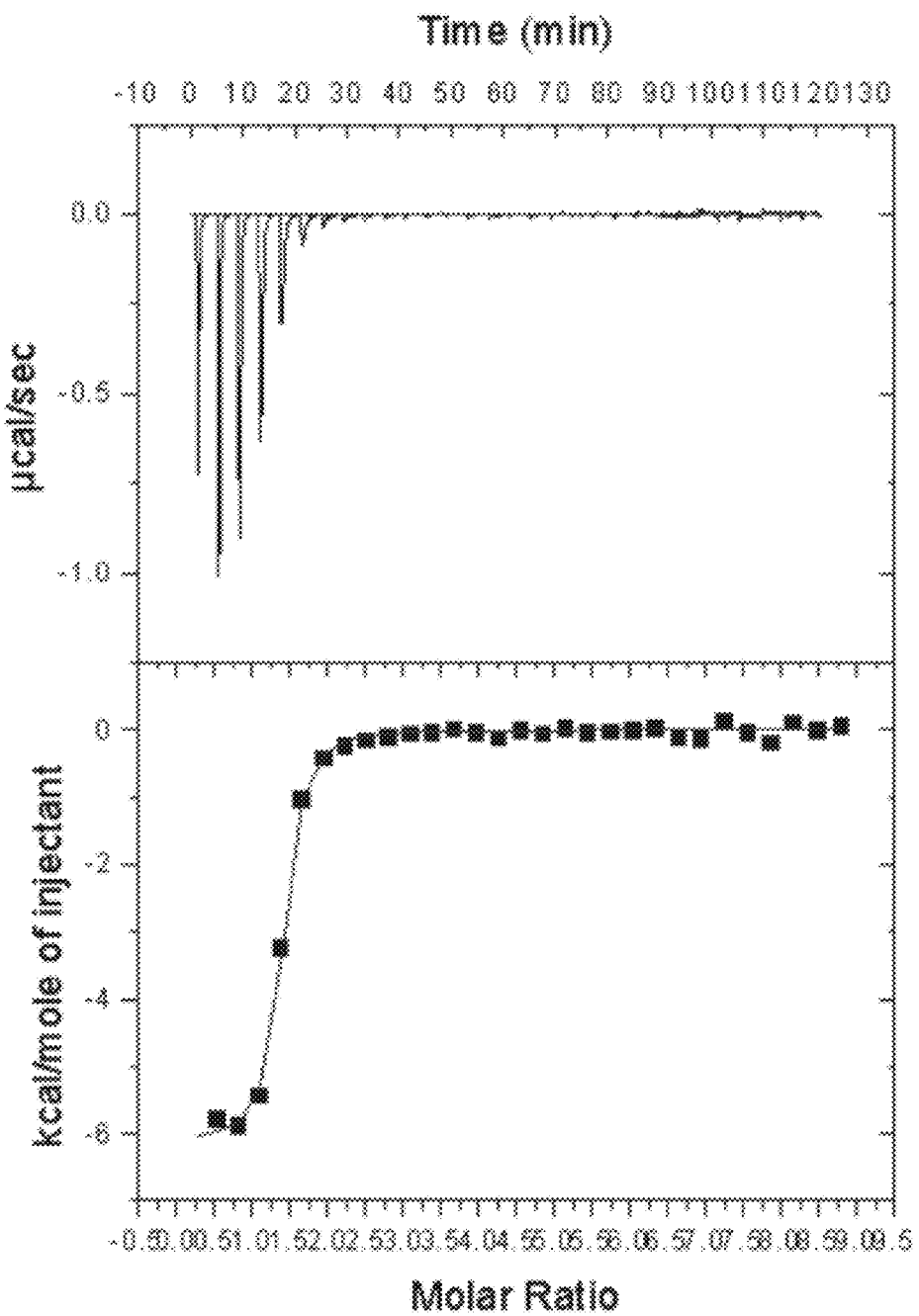
FIG. 11. Isothermal titration calorimetry of heparin-peptide interaction. The top panels show the differential power time course. Raw data for sequential 6-μl injections of each synthetic peptide in PBS buffer at 25° C. TAT (positive control), B, R1 (negative control), C, C1, and D, D1 into the sample cell containing 1.4 ml HMWH solution (10-20 μM). The total heat released in each injection is proportional to the area under the corresponding peak. The lower panels show a fit of the integrated areas based on peptide binding. The solid line represents a non-linear least squares of the reaction heat for the injection.
Figure 11:
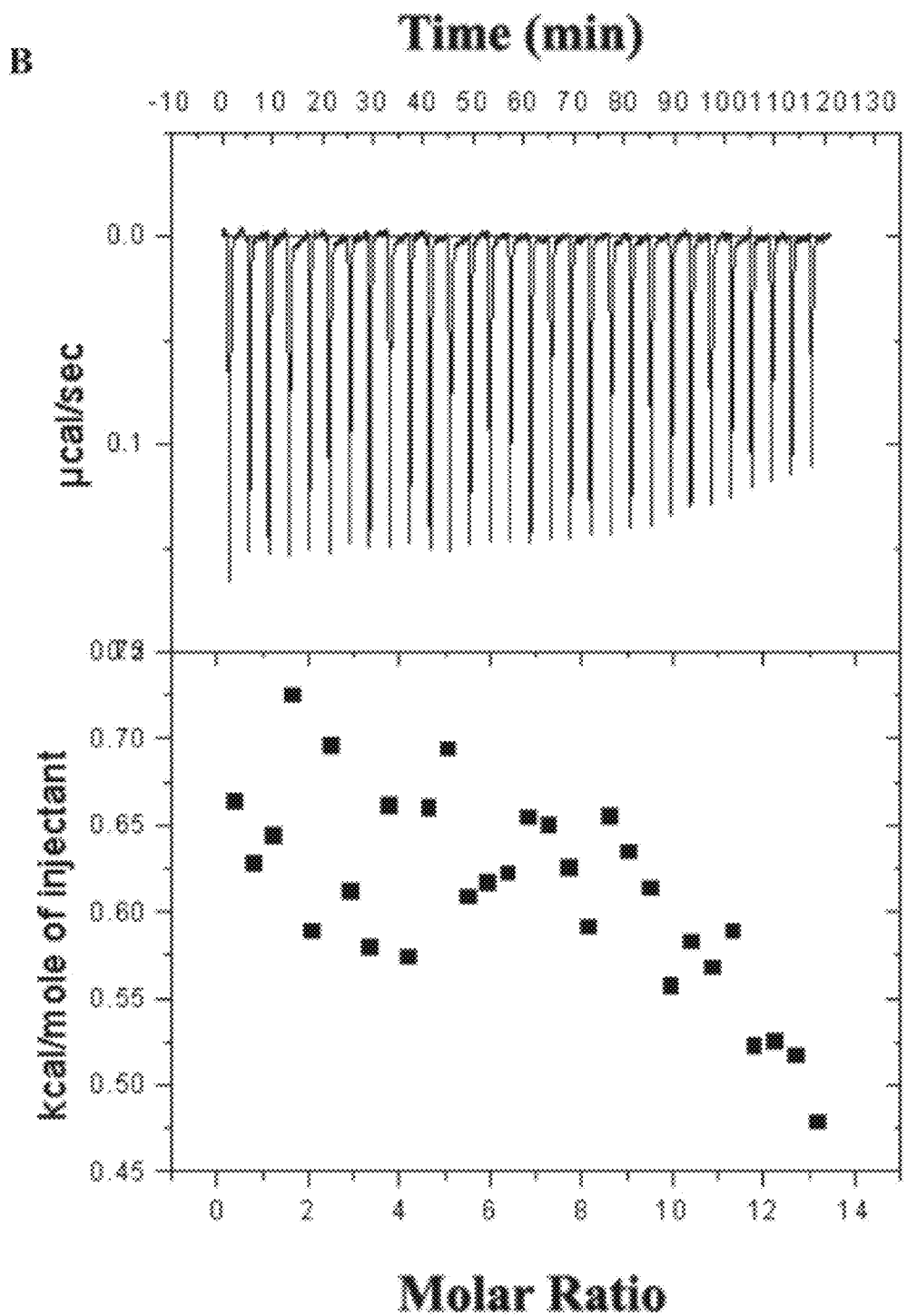
Figure 11:
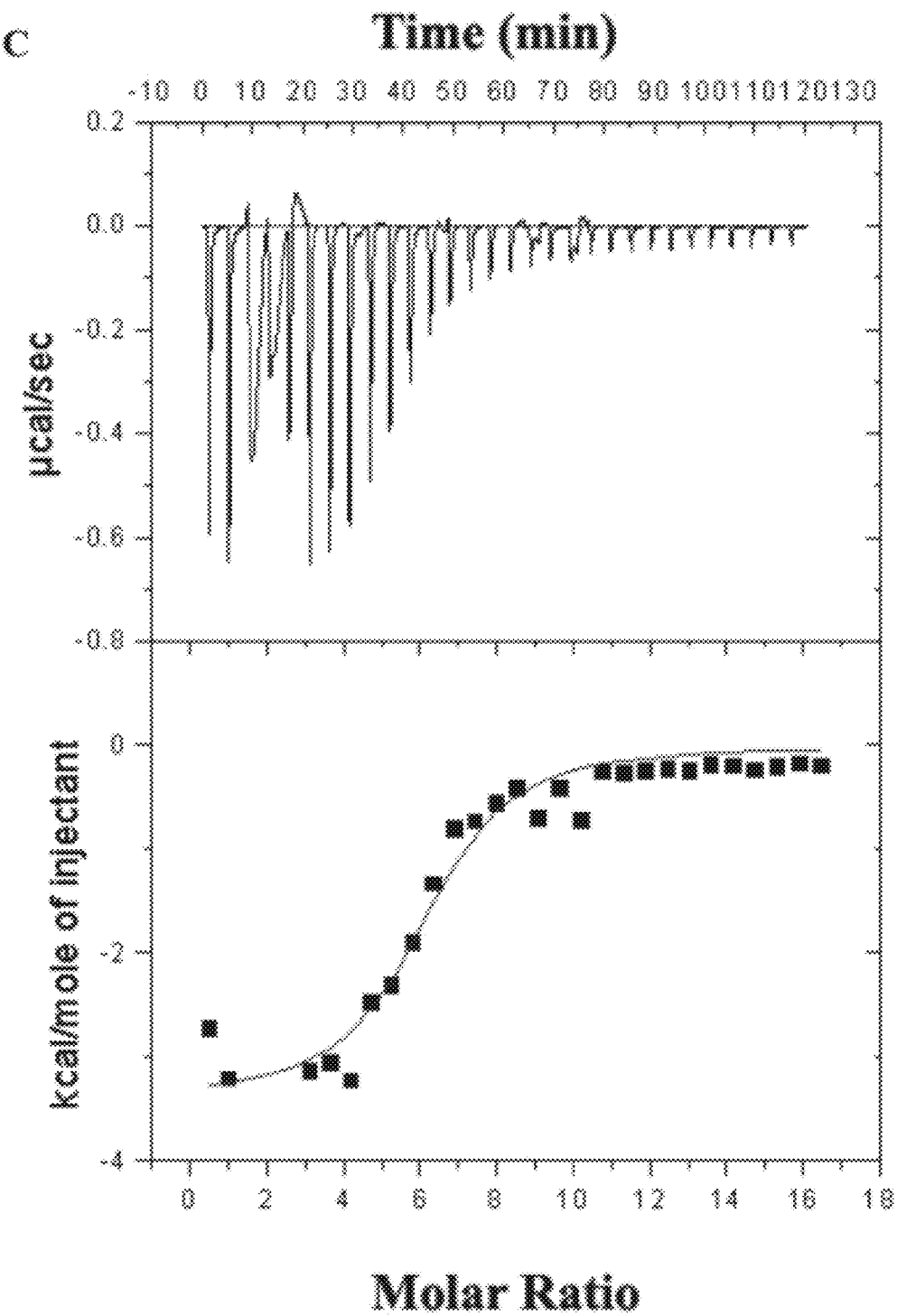
Figure 11:
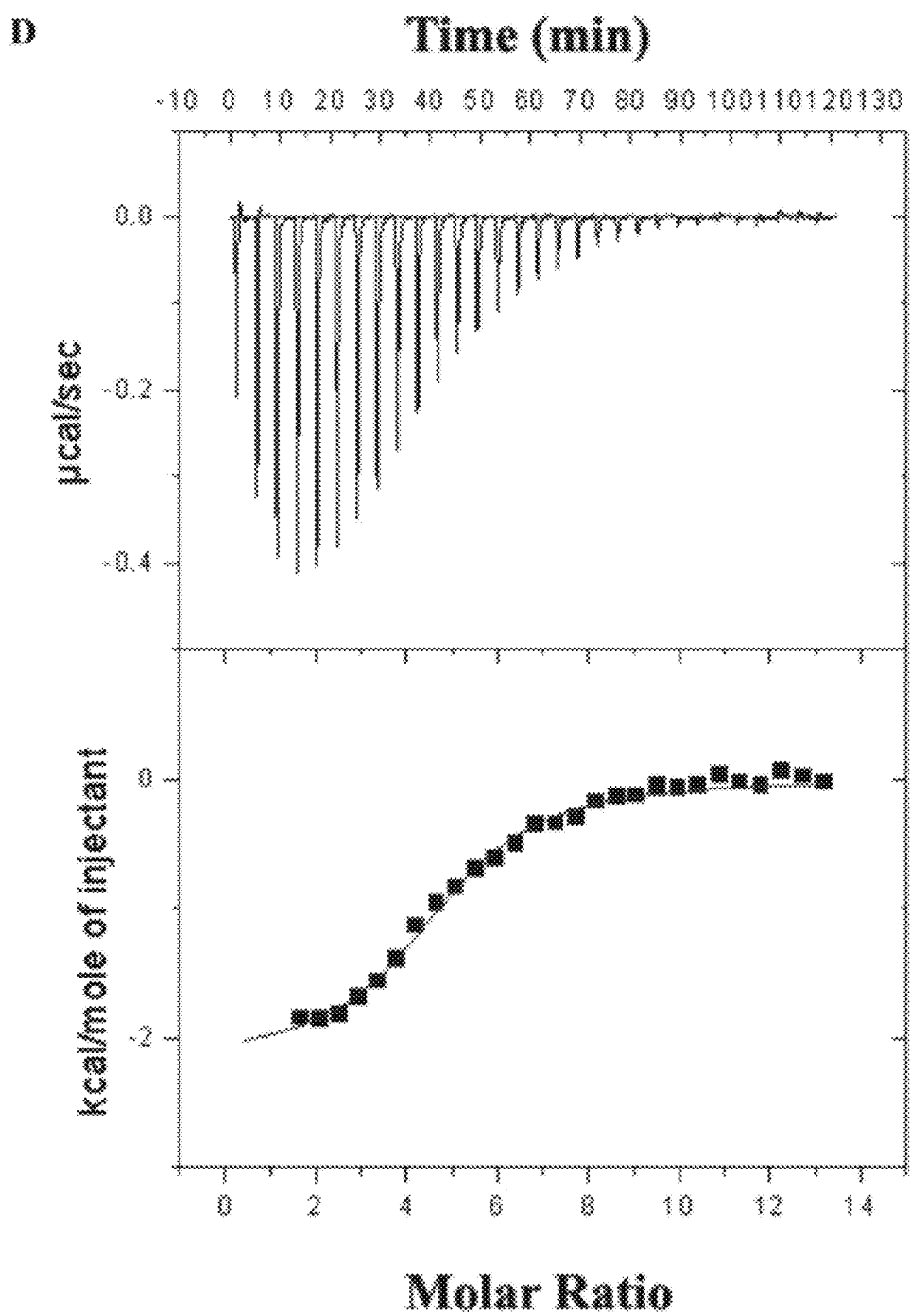

Characterization of Association Between Synthetic Heparin Binding Peptides and HMWH In general exothermal reaction takes place upon molecular binding between synthetic peptide and HMWH. As expected, the positive control TAT (SEQ ID NO: 6) peptide showed significant exothermal reaction mode employing ITC (FIG. 11A), whereas the negative control R1 (SEQ ID NO: 5) peptide revealed no heat release (FIG. 11B), strongly suggesting that no binding occurred between the test molecules. As for the synthetic C1 (SEQ ID NO: 3) and D1 (SEQ ID NO: 4) peptides, exothermal reaction modes were clearly observed (FIGS. 11C-D). These data further proved that peptide motifs C1 (SEQ ID NO: 3) and D1 (SEQ ID NO: 4) acted as crucial in vitro HMWH binding sites residing in human eosinophil RNases.

Example 11

Growth Inhibitory Effect of ECP

The inhibition of lymphocyte and mammalian cell growth by ECP has been reported (Fan, T. C., et al. (2007) Traffic 8, 1778-1795; Maeda, T., et al. (2002) European Journal of Biochemistry 269, 307-316). As a physiological test, the cytotoxicity of ECP mt1 was monitored by MTT assay. The effect of ECP on the cell growth was determined by a colorimetric assay using 3-(4,5-dimethylthiazol-2-yl)-2,5-diphenyltetrazolium bromide (MTT) (US Biological, MA, USA). Cells were plated in a 96-well plate (5000 cells/well) and incubated at 37° C. overnight. Each sample was incubated with the indicated concentration (1-100 µM) of ECP. Fortyeight hours after treatment with ECP, MTT was added, and cell growth was monitored at $A_{570}$ to measure the mitochondrial-dependent formation of a colored product.

Figure 12:
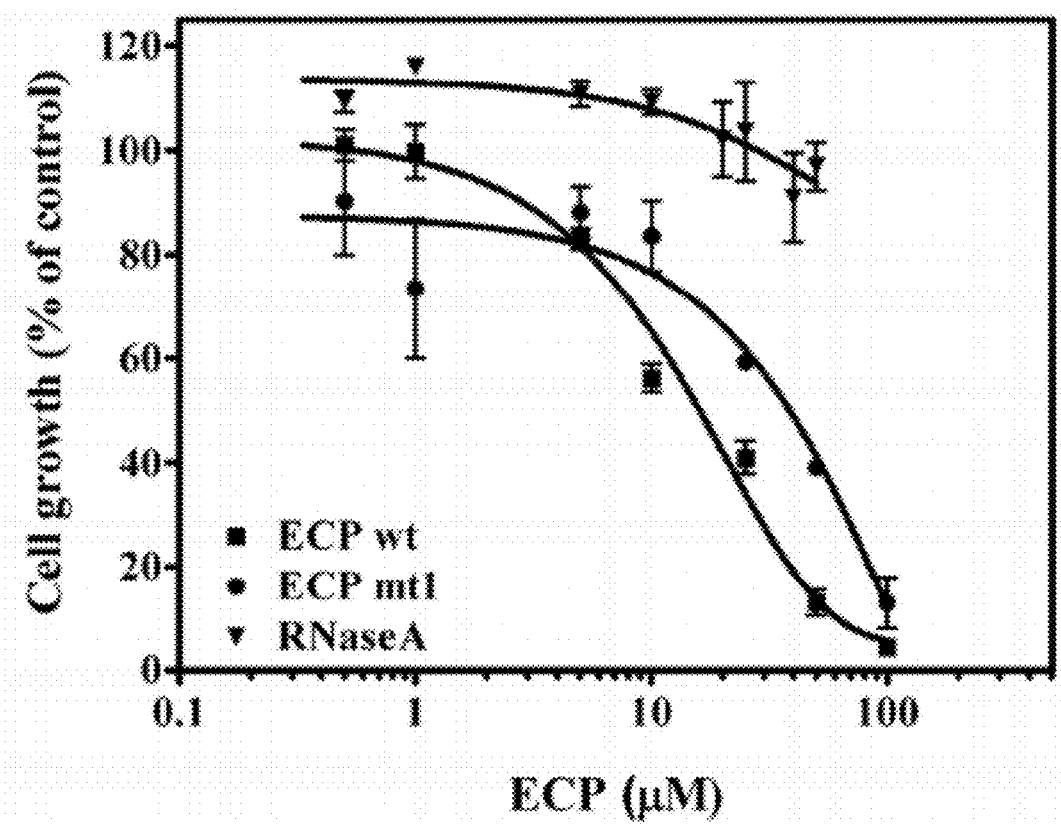
FIG. 12. Cytotoxicity of wild-type and mutant ECP. Beas-2B cells were incubated with increasing concentrations of wild-type and mt1 ECP at 37° C. for 48 h, followed by the MTT assay. The error bars show standard deviation among triplicate experiments.

As compared with wild-type ECP, ECP mt1 (R34A/W35A/R36A/K38A) exhibited a 2- to 3-fold increased $IC_{50}$ value toward the Beas-2B cell line (FIG. 12, Table III). Thus, ECP mt1 without the key heparin binding sequence motif appears to be less cytotoxic than wild-type ECP, presumably due to a lesser interaction with the cell surface, which in turn leads to less endocytosis.

TABLE III $IC_{50}$ values for cytotoxic ECP

| Protein | $IC_{50}$ (μM) |
|---|---|
| ECP wt[a] | 16.05 |
| ECP mt1 | 38.52 |

[a]Data taken from reference.(Fan, T. C., et al. (2007) Traffic 8, 1778-1795)

Example 12

Immunohistochemical Localization of ECP

To better understand the possible cellular targets of ECP, recombinant mature ECP was injected into the rat circulation through the tail vein.

Adult specific-pathogen-free (SPF) Sprague-Dawley rats (Narl:SD) with body weight (BW) of 200-300 g, were purchased and maintained at the National Laboratory Animal Center (NLAC) in Taiwan. The rats were separated into three groups. In group 1, each rat was injected with 5 nmol of ECP through the tail vein. In group 2, each rat was co-injected with heparin (FRAGMIN®, average MW 6000, 5000 IU/0.2 ml) and 5 nmol of ECP. In group 3, each rat was injected with 5 nmol of MBP as the negative control. All animals were sacrificed using $CO_2$ narcosis 1 h after the injection of these agents. The lung and trachea of these rats were taken and immediately fixed with 10% neutral buffered formaldehyde. The tissue samples were processed by routine methods to prepare paraffin wax-embedded block. These blocks were then sectioned into 6-μm slices. All tissue sections were examined using the Super Sensitive Non-Biotin HRP Detection System (BioGenex Laboratories, San Ramon, Calif.) as described (Liang, C. T., et al. (2007) Journal of comparative pathology 136, 57-64). Briefly, the mouse anti-ECP or anti-MBP monoclonal antibody was used as the primary antibody. Antigen unmasking was performed by immersion of sections in 5% Trilogy (Cell Marque, Rocklin, Calif.) antigen unmasking solution in Milli-Q water and boiled at 121° C. Endogenous peroxidase activity was quenched with hydrogen peroxide (3%) in methanol. These sections were then incubated in Power Block solution, and mouse anti-ECP or anti-MBP at 1/200 dilution was applied and left for 24 h. The sections were incubated with Super Enhancer reagent, followed by Polymer-HRP reagent, and then incubated with 3-amino, 9 ethylcarbazole chromogen solution. The sections were finally counterstained with Mayer's hematoxylin and mounted with Super Mount permanent aqueous mounting media prior to examination with a light microscope (Zeiss-Axioplan, Germany).

Figure 13:
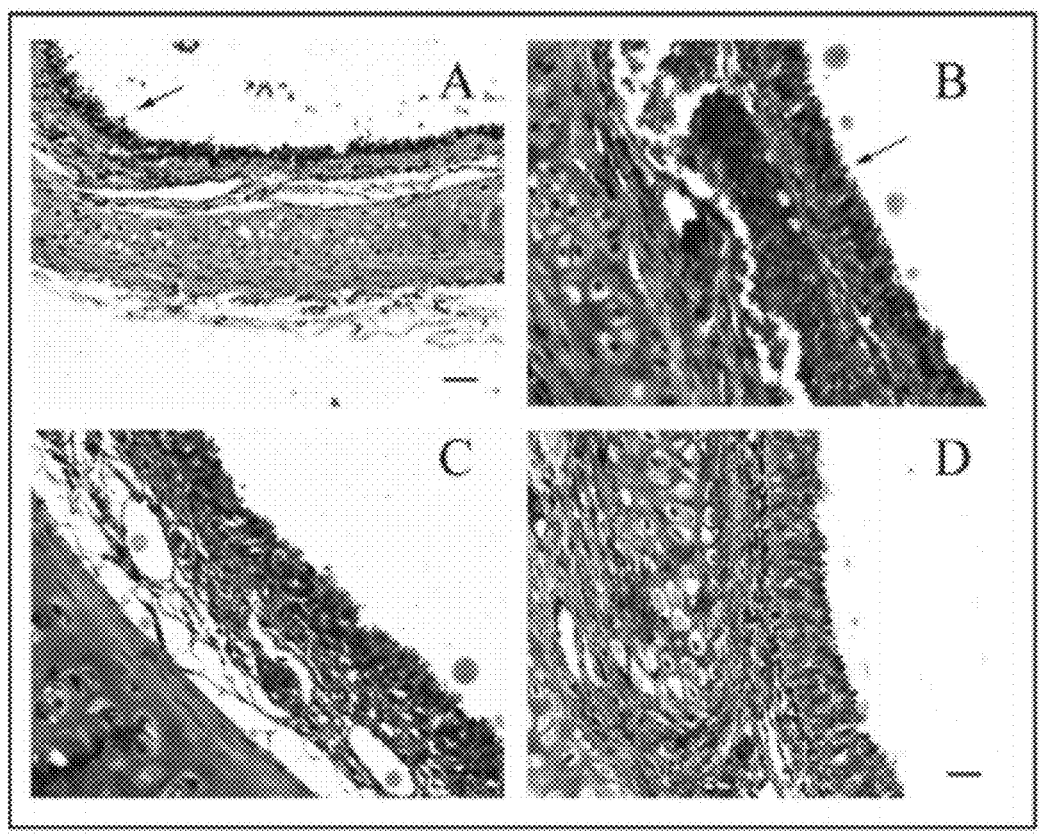
FIG. 13. Immunohistochemical localization of ECP using the Super Sensitive Non-Biotin HRP Detection System. Representative immunohistochemical staining patterns. ECP (red color) was detected in tracheo-epithelial cells (arrow) and cartilage cells 1 hr post-iv injection (A, B). Decreased ECP signal was observed in tracheo-epithelial cells when ECP was co-injected with heparin (C). A control section of lung tissue subjected to MBP injection was used as a negative control. Magnification: A, 200×; B, C, and D, 400×. Scale bars: 20 μm.

Immunohistochemical localization showed strong internalization of ECP in the tracheo- and broncho-epithelial cells 1 h post-injection (FIGS. 13A-B). ECP internalizaiton was reduced when co-injection with heparin was carried out (FIG. 13C). For the negative control, no MBP signal was detected in tracheo- and broncho-epithelial cells, despite the MBP signal that could be detected in circulating blood (FIG. 13D).

Example 13

Airway Inflammation Reduction in eIN Mice

Preparation of mite protein Crude extract of mite Der p was purchased from Greer Lab (Lenior, N.C., USA). The mite protein was extracted from the crude extract with phosphate buffered saline (PBS) using a glass-glass homogenizer (Kontes Glass Company, Vineland, N.J., USA). The mite protein concentration was then determined using Bradford assay (Bio-Rad protein Assay; Bio-Rad, Hercules, Calif., USA).

Animals Study protocol Female Balb/c mice 8 weeks of age were obtained from the National Laboratory Breeding Research Center in Taiwan and were raised in a specific pathogen-free environment. The mice were divided into six groups: (1) control, (2) mite intra-tracheal (mIT) alone, (3) $ECP^{32-41}$ (SEQ ID NO: 9) intranasal, (eIN) alone, (4) pre-treated group: eIN+mIT, (5) post-treated group: mIT+eIN and (6) pre+post-treated group eIN+mIT+eIN. Mite crude extract allergen (1.6 μg/μl) was prepared and well emulsified in complete Freund's adjuvant (CFA; Sigma, St Louis, Mo., USA) at a ratio of 1:1 at 4° C. The mIT, eIN and eIN+mIT groups were immunized subcutaneously with 50 μl emulsified mite protein on day 1 and day 8.

Ten microliter of mite crude extract allergen (5 μg/μl), dissolved in PBS, and was used for each mouse on day 15. Each mouse was anesthetized for about 1 min. With the exception of control group, all groups receiving mIT were immunized with mite crude extract allergen on day 1 and day 8, then mite crude extract allergen intra-tracheally on day 15. Ten microliters of $ECP^{32-41}$ (SEQ ID NO: 9) (20 μM) was then administered intranasally to mice. Groups 3 and 6 received eIN from day 1 to 22, group 4: day 1 to 15 (before mIT), and group 5: day 15 (post-mIT) to day 22. Then mice were sacrificed on day 23. The animal use protocol was reviewed and approved by the Institutional Animal Care and Use Committee (IACUC Approval No: La-95279).

Measurement of pause enhancement (Penh) Airway responsiveness was measured in mice on day 22, 1 h after the last challenge in conscious, spontaneously breathing mice using a whole-body plethysmography (WBP) system (Buxco, Wilmington, N.C., USA). Mice were placed in chamber and allowed to settle for 3 to 5 min, and the hamber-pressure-time wave was continuously measured via a transducer connected to a computer data-acquisition system. After baseline Penh reading for over 3 min, mice were serially exposed to increasing concentrations of nebulized methacholine (MCh) (0, 6.25, 12.5 and 25 mg/ml) (Sigma-Aldrich, St. Louis, Mo.) in PBS by inhalation for 1 min. Penh values, which were measured as changes in enhanced pause, tidal volume (Vt), and breading frequency (breaths/minute) for the first 3 min after the end of MCh nebulization were averaged and used to compare responses among these 6 groups.

Figure 14:
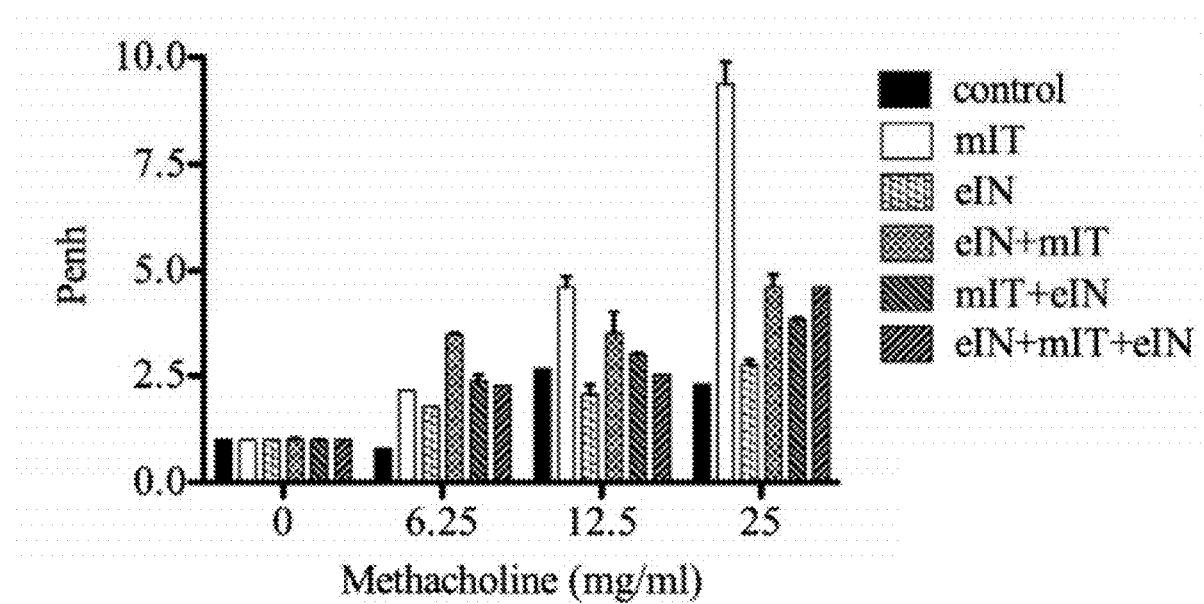
FIG. 14. The airway hyperreactivity (AHR) in mice treated with ECP[32-41] (SEQ ID NO: 9) during allergen sensitization. Values were expressed as means±standard error of the means (SEMs) of 4 mice.

In this study, the regulatory effects of $ECP^{32-41}$ (SEQ ID NO: 9) on mite-induced airway inflammation in murine asthma model were evaluated. The mice were divided into six groups: (1) control, (2) mite intra-tracheal (mIT) alone, (3) $ECP^{32-41}$ (SEQ ID NO: 9) intranasal, (eIN) alone, (4) pre-treated group (eIN+mIT), (5) post-treated group (mIT+eIN) and (6) pre+post-treated group (eIN+mIT+eIN). Serial changes of pause enhancement (Penh) in these six groups after methacholine stimulations were shown in FIG. 14. eIN+mIT, mIT+eIN and eIN+mIT+eIN could significantly decrease airway hyperreactivity (AHR) in mice as assessed by their response to increase the dose of inhaled methacholine. mIT group showed much higher Penh/baseline ratio change after methacholine stimulation at concentrations of 12.5 and 25 mg/ml, both p values were below 0.001. eIN+mIT+eIN and eIN groups revealed similar response to the control group. eIN+mIT and mIT+eIN groups showed lower methacholine stimulation at 25 mg/ml but not at 12.5 mg/ml. In conclusion, ECP$^{32-41}$ (SEQ ID NO: 9) exerts therapeutic effect in down-regulation of allergen-induced airway inflammation and may serve an alternative treatment with current anti-asthma medications for asthma patients.

Example 14

ECP$^{32-41}$ (SEQ ID NO: 9) Reduced Asthma Pathology in Mite-Induced Mice

Histopathological analysis Lung sections stained with hematoxylin and eosin (H&E) were assigned a unit value for alveolar, peri-bronchiolar and total inflammation by computing the means of three independent scores for three randomly selected view-fields. Each section was interpreted by two physicians (Fu L S and Lin H K) independently and scoring system for airway inflammation was applied (Ford, J. G., Rennick, D., Donaldson, D. D., Venkayya, R., McArthur, C., Hansell, E., Kurup, V. P., Warnock, M., and Grunig, G. (2001) *J Immunol* 167, 1769-1777). Total inflammatory scores were determined as the sum of the peri-bronchiolar and alveolar inflammatory scores.

Figure 15:
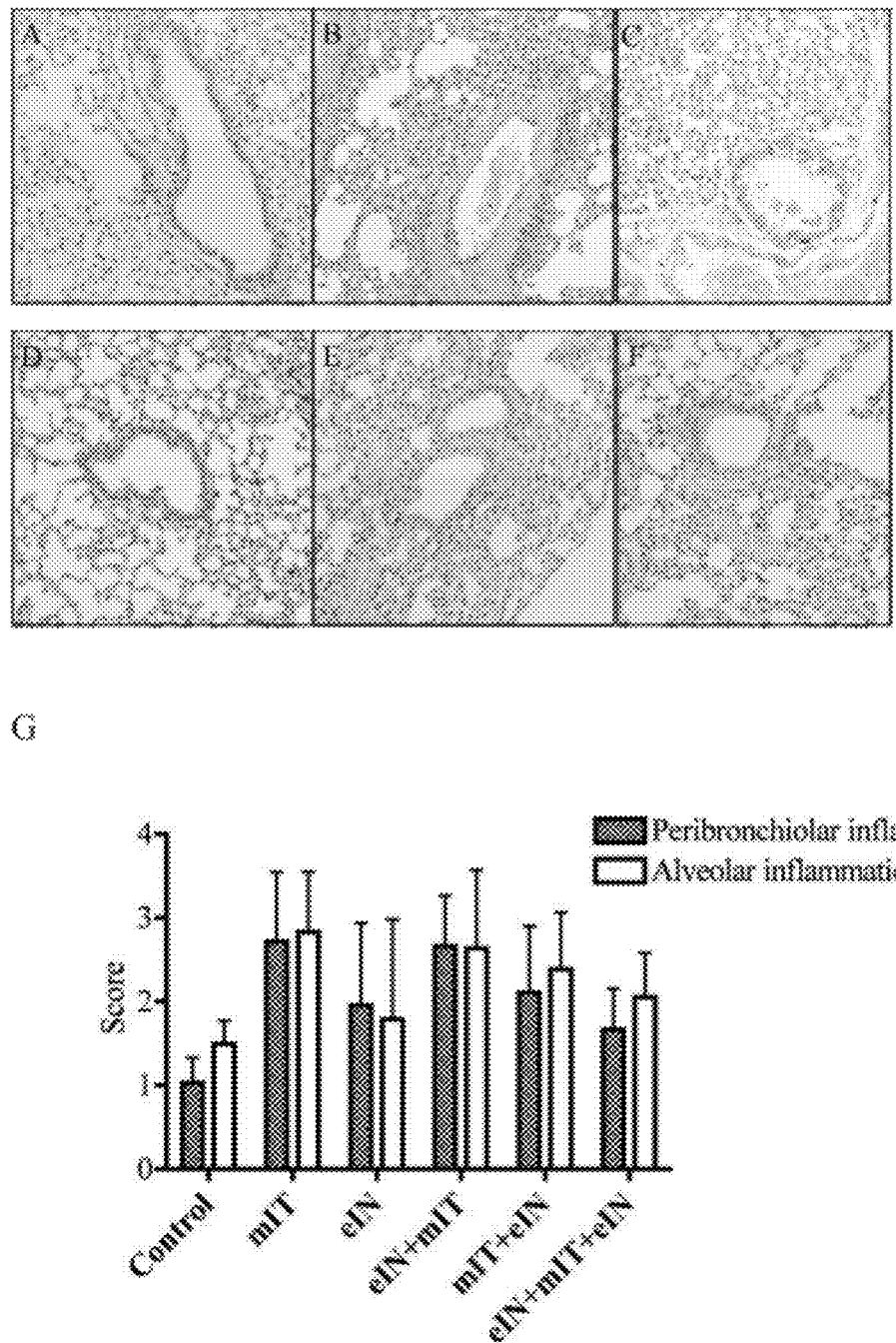
FIG. 15. Tissue pathology staining in mice. 5-μm formalin-fixed lung sections were stained with H & E in (A) control (B) mIT, (C) eIN, (D) eIN+mIT, (E) mIT+eIN and (F) eIN+mIT+eIN mice. (G) Peribronchial and alveolar inflammation scores.

To determine whether suppression of airway cellular infiltration represented a more general down-modulation of pathology, lung histological sections were compared in six groups of mice. Haematoxylin and eosin (H & E) staining was used to characterize peri-bronchiolar and alveolar inflammation.

eIN-treated mice (FIG. 15C) did not demonstrate allergic airway inflammatory pathologies including infiltration of inflammatory cells, mast cell degranulation and goblet cell proliferation as control (FIG. 15A). In asthmatic mice, airway challenge led to a dense peri-bronchiolar inflammatory infiltration of lymphocytes and production of mononuclear and polymorphonuclear cells with epithelial shedding and extended columnal cells (FIG. 15B). Tissue inflammation was greatly reduced with less peri-bronchial and perivascular cellular infiltration and mucin staining in eIN+mIT (FIG. 15D), mIT+eIN (FIG. 15E) and eIN+mIT+eIN (FIG. 15F) mice. In addition, peribronchial and alveolar inflammation scores were collected and analyzed in each group as shown in FIG. 15G. Although there were also peri-bronchial inflammatory cells in eIN+mIT+eIN group, pathology of this group was still significantly milder than mIT group (p<0.0001). The alveolar score of eIN+mIT+eIN group was lower than that of mIT group (p=0.009). In addition, eIN+mIT+eIN had a more potently suppressive effect on peri-bronchiolar and alveolar inflammation than eIN+mIT and mIT+eIN group.

Example 15

ECP$^{32-41}$ (SEQ ID NO: 9) Reduced Mite-Specific Plasma IgE and IgG2a Levels

Measurement of Der p-specific IgE and IgG2a antibodies All BALB/c mice were sacrificed, and the blood was obtained from inferior vena cava on day 23. Plasma Der p-specific IgE and IgG2a levels were measured by enzyme-linked immunosorbent assay (ELISA). The microplates were coated with mite crude extract allergen (50 μg/μl) overnight at 4° C. The plates were blocked with 10% fetal bovine serum (FBS) in PBS at room temperature for 2 h. The plasma samples were added to the wells of the microplates and incubated at 4° C. overnight. After washing with PBS containing 0.05% Tween 20 (PBST), the plates were incubated with Der p-specific anti-IgE antibody (Abcam, UK) or anti-Ig G2a antibody (Abcam, UK) at room temperature for 2 h. The plates were then washed twice with PBST before incubated with horseradish-peroxidase (HRP) streptavidin conjugate (Zymed, Calif., USA) at room temperature for 1 h. The plates were then incubated with 3,3',5,5'-tetramethylbenzidine (TMB) substrate (BD Biosciences, Franklin Lakes, N.J.) in the dark at room temperature for 30 min and the absorption at 450 nm was measured using ELISA reader. Since no Der p-specific IgE or IgG2a standard was available, all samples were tested at the same time and results were expressed as an optical density (O.D.) value. The final mean O.D. level of the control group was defined as 100% in final presentation.

Figure 16:
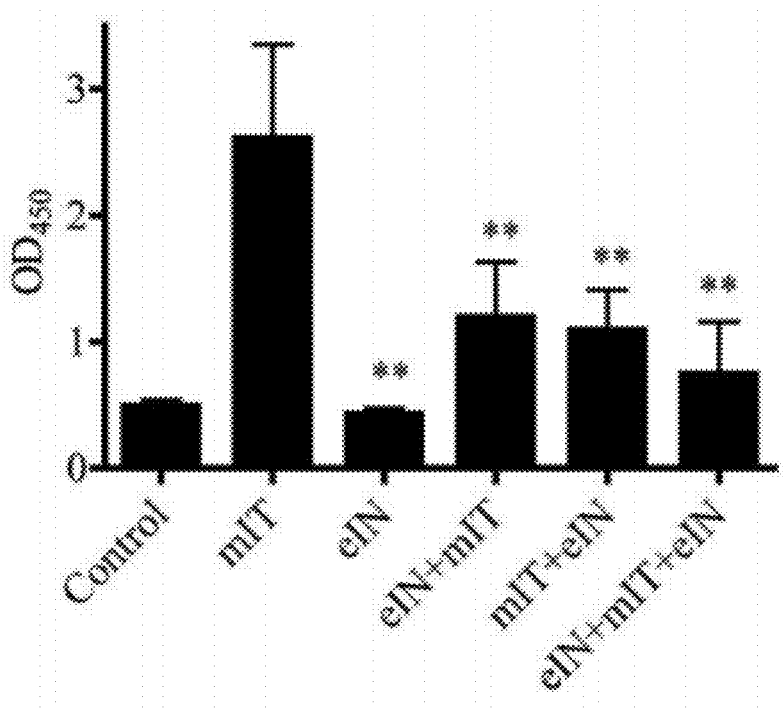
FIG. 16. Specific Der p2 antibody responses in mice. Serum from a group of six mice was assayed for the indicated antibody. Data represent one of three independent experiments. (A) Specific Der p2 IgE antibody (B) Specific Der p2 IgG2a antibody. Each data was expressed as the mean±S.D., n=3. **, P<0.01.
Figure 16:
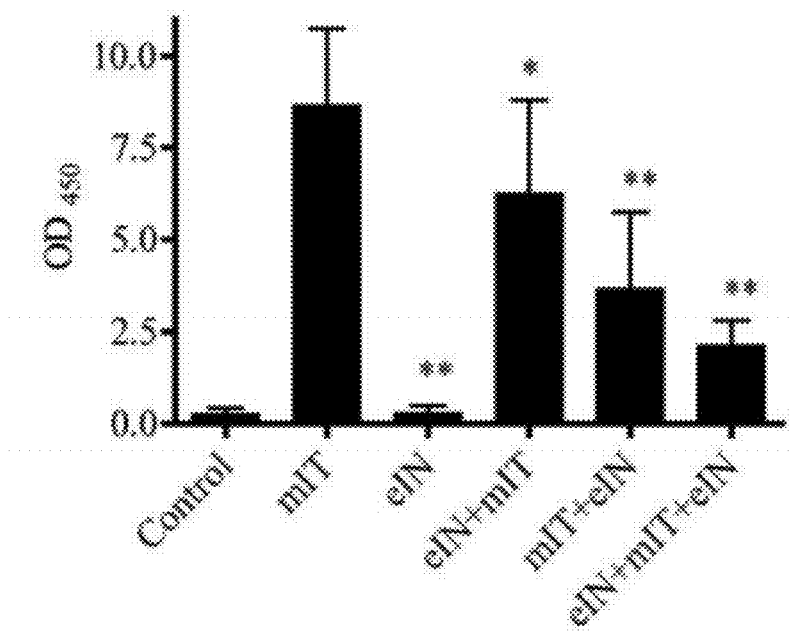

To further analyze the inhibitory effect of ECP$^{32-41}$ (SEQ ID NO: 9) on airway inflammation, specific Der p2 IgE and IgG2a levels in asthma mouse model were measured. FIGS. 16A and B showed mite-specific plasma IgE and IgG2 levels in these 6 groups. The mIT group had significantly higher IgE than eIN+mIT, mIT+eIN and eIN+mIT+eIN groups (FIG. 16A). However, only mIT+eIN and eIN+mIT+eIN had much lower IgG2a than mIT group, although eIN+mIT group had lower IgG2a than mIT group (FIG. 16B). ECP$^{32-41}$ (SEQ ID NO: 9) reduced the key molecules, specific Der p2 IgE and IgG2a, strongly providing a mechanistic explanation for the down-regulation of airway inflammation in asthma mouse.

The invention claimed is:

1. A method for treating asthma in a subject by reducing cytotoxicity of eosinophil derived toxins in bronchial epithelial cells of the subject, wherein the eosinophil derived toxin is eosinophil cationic protein, the method comprising:
   (a) preparing a pharmaceutical composition comprising an isolated peptide consisting of the amino acid sequence of SEQ ID NO: 9; and
   (b) administering an effective amount of the composition to the subject.

2. The method of claim 1, wherein the cytotoxicity of eosinophil derived toxins is reduced by reducing endocytosis of eosinophil derived toxins.

3. The method of claim 2, wherein the reducing endocytosis of eosinophil derived toxins is achieved by the peptide competing with eosinophil derived toxins for cellular binding.

4. The method of claim 1, wherein the subject is a mammal.

5. The method of claim 4, wherein the mammal is a human.

6. The method of claim 1, wherein the composition further comprises a pharmaceutically acceptable carrier.

7. The method of claim 1, wherein the administration is intranasal administration.

* * * * *